US008575098B2

(12) United States Patent
Rodríguez Cabello et al.

(10) Patent No.: US 8,575,098 B2
(45) Date of Patent: Nov. 5, 2013

(54) BIOPOLYMER, IMPLANT COMPRISING IT AND USES THEREOF

(75) Inventors: José Carlos Rodríguez Cabello, Valladolid (ES); Matilde Alonso Rodrigo, Valladolid (ES); Francisco Javier Arias Vallejo, Valladolid (ES); Alessandra Girotti, Valladolid (ES); Laura Martín Maroto, Valladolid (ES); Ana María Testera Gorgojo, Valladolid (ES)

(73) Assignee: Universidad de Valladolid, Valladolid (ES)

( * ) Notice: Subject to any disclaimer, the term of this patent is extended or adjusted under 35 U.S.C. 154(b) by 29 days.

(21) Appl. No.: 13/201,498

(22) PCT Filed: Feb. 16, 2010

(86) PCT No.: PCT/ES2010/070084
§ 371 (c)(1),
(2), (4) Date: Nov. 30, 2011

(87) PCT Pub. No.: WO2010/092224
PCT Pub. Date: Aug. 19, 2010

(65) Prior Publication Data
US 2012/0157393 A1 Jun. 21, 2012

(30) Foreign Application Priority Data
Feb. 16, 2009 (ES) .................................. 200900438

(51) Int. Cl.
*A61K 38/18* (2006.01)
*A61K 38/00* (2006.01)
*A61P 19/08* (2006.01)

(52) U.S. Cl.
USPC .......................................... 514/8.3; 514/16.7

(58) Field of Classification Search
None
See application file for complete search history.

(56) References Cited

U.S. PATENT DOCUMENTS

2005/0180945 A1 8/2005 Chaikof et al.

FOREIGN PATENT DOCUMENTS

WO 2008/033847 3/2008

OTHER PUBLICATIONS

Bromberg et al. "Temperature-responsive gels and thermogelling polymer matrices for protein and peptide delivery", Advanced Drug and Delivery Reviews, 1998, 31, 197-221, Elsevier Science B.V.
Arias et al. "Tailored recombiant elastin-like polymers for advanced biomedical and nano (bio) technological applications", Biotechnol Lett, 2006, 28, 687-695, Springer.
Chow et al. "Peptide-based Biopolymers in Biomedicine and Biotechnology", NIH Public Access., 2008, 62, 4, 125-155, Mater Sci Eng R Rep.
Peppas et al. "Hydrogels in pharmaceutical formulations" European Journal of Pharmaceutics and Biopharmaceutics, 2000, 50, 27-46, Elsevier Science B.V.
Gamisans et al. "Flurbiprofen-loaded nanospheres: analysis of the matrix structure by thermal methods"International Journal of Pharmaceutics, 1999, 179, 37-48, Elsevier Science B.V.
Hoffman et al. "Founder's Award, Sixth World Biomaterials Congress 2000, Kamuela, HI, May 15-20, 2000", 1-10, John Wiley & Sons, Inc.
Jeong et al. "New biodegradable polymers for injectable drug delivery systems", Journal of Controlled Release, 1999, 62, 109-114, Elsevier Science B.V.
Hatefi et al. "Biodegradable injectable in situ forming drug delivery systems", Journal of Controlled Release, 2002, 80, 9-28, Elsevier Science B.V.
Rodriguez-Cabello et al. "Biofunctional design of elastin-like polymers for advanced applications in nanbiotechnology", J. Biomater. Sci. Polymer Edn, 2007, 18, 3, 269-286, VSP.
Igartua el al. "Enhanced inmune response after subcutaneous and oral immunization with biodegradable PLGA microspheres", Journal of Controlled Release, 1998, 56, 63-73, Elsevier Science B.V.
Lee et al. "A Thermosensitive Pol(organophosphazene) Gel" Macromolecules, 2002, 35, 3876-3879, American Chemical Society.
Brannon-Peppas, "Controlled release of B-estradiol from biodegradable microparticles within the silicone matrix".
Sosnik et al. "Poly (ethylene glycol)-Poly(epsilon-caprolactone) Block Oligomers as Injectable Materials" Polymer, 2003, 44, 7033-7042, Elsevier Ltd.
Kawaguchi, "Functional polymer microspheres" Prog. Polym. Sci., 200, 1171-1210, Elsevier Ltd.
International Search Report dated May 31, 2010 for international application No. PCT/ES2010/070084.

*Primary Examiner* — Thomas Heard
(74) *Attorney, Agent, or Firm* — Garnder Groff Greenwald & Villanueva, PC

(57) ABSTRACT

The present invention relates to a biopolymer, bioactive and totally biocompatible, very fluid at ambient temperature, capable of gelling in a sudden manner at 37° C., forming a solid implant, structurally integral and continuous having high mechanical properties. The biopolymer comprises at least a bioactive domain capable of directing in a precise manner the formation of a solid or semisolid implant. Furthermore the invention relates to any of the nucleic acids encoding the amino acid sequence of the biopolymer, implants, pharmaceutically acceptable vehicles, uses thereof, and a method of synthesis thereof.

19 Claims, 11 Drawing Sheets

SEQUENCE LISTING

```
<160> NUMBER OF SEQ ID NOS: 27

<210> SEQ ID NO 1
<211> LENGTH: 5
<212> TYPE: PRT
<213> ORGANISM: Artificial Sequence
<220> FEATURE:
<223> OTHER INFORMATION: Synthetic construct of Peptide D

<400> SEQUENCE: 1

Val Pro Gly Val Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic construct of Peptide E

<400> SEQUENCE: 2

Val Pro Gly Glu Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct of Sequence 1 of peptide B

<400> SEQUENCE: 3
```

```
Val Gly Ile Pro Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct of Sequence 2 of peptide B

<400> SEQUENCE: 4

Val Gly Ala Pro Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic construct of Peptide G

<400> SEQUENCE: 5

Val Pro Gly Ile Gly
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic construct of Sequence C

<400> SEQUENCE: 6

Ala Val Thr Gly Arg Gly Asp Ser Pro Ala Ser Ser
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetic construct of Alternative domain 1,
      peptide H

<400> SEQUENCE: 7

Arg Glu Asp Val
1

<210> SEQ ID NO 8
<211> LENGTH: 4
<212> TYPE: PRT
<213> ORGANISM: Artificial Sequence
<220> FEATURE:
<223> OTHER INFORMATION: Synthetic construct of Alternative domain 2,
      peptide H

<400> SEQUENCE: 8

Asp Gly Glu Ala
1

<210> SEQ ID NO 9
<211> LENGTH: 5
<212> TYPE: PRT
<213> ORGANISM: Artificial Sequence
<220> FEATURE:
<223> OTHER INFORMATION: Synthetic construct of Alternative domain 3,
      peptide H
```

```
<400> SEQUENCE: 9

Tyr Ile Gly Ser Arg
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic construct of Alternative domain 4,
      peptide H

<400> SEQUENCE: 10

Gln Ala Ala Ser Ile Lys Val Ala Val
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic construct of Sequence of SNA15

<400> SEQUENCE: 11

Asp Asp Asp Glu Glu Lys Phe Leu Arg Arg Ile Gly Arg Phe Gly
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Synthetic construct of Sequence with affinity
      for gold

<400> SEQUENCE: 12

Met His Gly Lys Thr Gln Ala Thr Ser Gly Thr Ile Gln Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic construct of Sequence with affinity
      for silver

<400> SEQUENCE: 13

Ala Tyr Ser Ser Gly Ala Pro Pro Met Pro Pro Phe
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic construct of Sequence with affinity
      for platinum

<400> SEQUENCE: 14

Asp Arg Thr Ser Thr Trp Arg
1               5

<210> SEQ ID NO 15
<211> LENGTH: 12
<212> TYPE: PRT
<213> ORGANISM: Artificial Sequence
<220> FEATURE:
```

-continued

<223> OTHER INFORMATION: Synthetic construct of Sequence with affinity
      for silicon

<400> SEQUENCE: 15

Lys Pro Ser His His His His His Thr Gly Ala Asn
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic construct

<400> SEQUENCE: 16

His Thr Gln Asn Met Arg Met Tyr Glu Pro Trp Phe
1               5                   10

<210> SEQ ID NO 17
<211> LENGTH: 75
<212> TYPE: DNA
<213> ORGANISM: Artificial Sequence
<220> FEATURE:
<223> OTHER INFORMATION: Synthetic construct of Sequence of block D2 E
      D2

<400> SEQUENCE: 17
gtaccaggtg ttggtgttcc gggtgttggc gtgccgggcg aaggcgtgcc gggtgttggt     60
gttccgggtg taggg                                                     75

<210> SEQ ID NO 18
<211> LENGTH: 300
<212> TYPE: DNA
<213> ORGANISM: Artificial Sequence
<220> FEATURE:
<223> OTHER INFORMATION: Synthetic construct of Sequence for B20 of
      biopolymer A

<400> SEQUENCE: 18
gtaggtatcc cgggcgttgg tatcccgggc gtgggtattc cgggcgttgg tatcccgggc     60
gtaggtatcc caggcgttgg tatcccgggc gtgggtatcc cgggcgttgg tattccgggc    120
gtgggtatcc cgggcgttgg tatccctggt gtaggtatcc cgggcgttgg tatcccgggc    180
gtgggtattc cgggcgttgg tatcccgggc gtaggtatcc caggcgttgg tatcccgggc    240
gtgggtatcc cgggcgttgg tattccgggc gtgggtatcc cgggcgttgg tatccctggt    300

<210> SEQ ID NO 19
<211> LENGTH: 336
<212> TYPE: DNA
<213> ORGANISM: Artificial Sequence
<220> FEATURE:
<223> OTHER INFORMATION: Synthetic construct of Sequence of G10 H G10

<400> SEQUENCE: 19
gtaccgggca tcggtgttcc gggcattggt gtgccgggca tcggtgttcc gggcattggt     60
gtgccgggca tcggtgtgcc aggcattggt gtgccgggca tcggtgttcc gggcattggt    120
gtgccgggca tcggtgtgcc aggcattggt gcagtaaccg gtcgtgggga ttctcctgcg    180
tccagcgtcc cgggcatcgg tgttccgggc attggtgtgc cggcatcgg tgttccgggc    240 attggtgtgc cggcatcgg tgtgccaggc attggtgtgc cggcatcgg tgttccgggc    300 attggtgtgc caggcatcgg tgtgccgggc attggt                              336

```
<210> SEQ ID NO 20
<211> LENGTH: 18
<212> TYPE: DNA
<213> ORGANISM: Artificial Sequence
<220> FEATURE:
<223> OTHER INFORMATION: Synthetic construct of Additional sequence 5'

<400> SEQUENCE: 20
atggaatccc tgctgccg                                                    18

<210> SEQ ID NO 21
<211> LENGTH: 3996
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(3996)

<400> SEQUENCE: 21
```

| | | | | | | | | | | | | | | | | |
|---|---|---|---|---|---|---|---|---|---|---|---|---|---|---|---|---|
| atg | gaa | tcc | ctg | ctg | ccg | gta | cca | ggt | gtt | ggt | gtt | ccg | ggt | gtt | ggc | 48 |
| Met | Glu | Ser | Leu | Leu | Pro | Val | Pro | Gly | Val | Gly | Val | Pro | Gly | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | ccg | ggc | gaa | ggc | gtg | ccg | ggt | gtt | ggt | gtt | ccg | ggt | gta | ggg | gta | 96 |
| Val | Pro | Gly | Glu | Gly | Val | Pro | Gly | Val | Gly | Val | Pro | Gly | Val | Gly | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| cca | ggt | gtt | ggt | gtt | ccg | ggt | ggc | gtg | ccg | ggc | gaa | ggc | gtg | ccg | | 144 |
| Pro | Gly | Val | Gly | Val | Pro | Gly | Gly | Val | Pro | Gly | Glu | Gly | Val | Pro | | |
| | 35 | | | | | 40 | | | | | 45 | | | | | |

| | | | | | | | | | | | | | | | | |
|---|---|---|---|---|---|---|---|---|---|---|---|---|---|---|---|---|
| ggt | gtt | ggt | gtt | ccg | ggt | gta | ggg | gta | cca | ggt | gtt | ggt | gtt | ccg | ggt | 192 |
| Gly | Val | Gly | Val | Pro | Gly | Val | Gly | Val | Pro | Gly | Val | Gly | Val | Pro | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| gtt | ggc | gtg | ccg | ggc | gaa | ggc | gtg | ccg | ggt | gtt | ggt | gtt | ccg | ggt | gta | 240 |
| Val | Gly | Val | Pro | Gly | Glu | Gly | Val | Pro | Gly | Val | Gly | Val | Pro | Gly | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggg | gta | cca | ggt | gtt | ggt | gtt | ccg | ggt | gtt | ggc | gtg | ccg | ggc | gaa | ggc | 288 |
| Gly | Val | Pro | Gly | Val | Gly | Val | Pro | Gly | Val | Gly | Val | Pro | Gly | Glu | Gly | |
| | | | 85 | | | | | 90 | | | | | 95 | | | |

| | | | | | | | | | | | | | | | | |
|---|---|---|---|---|---|---|---|---|---|---|---|---|---|---|---|---|
| gtg | ccg | ggt | gtt | ggt | gtt | ccg | ggt | gta | ggg | gta | cca | ggt | gtt | ggt | gtt | 336 |
| Val | Pro | Gly | Val | Gly | Val | Pro | Gly | Val | Gly | Val | Pro | Gly | Val | Gly | Val | |
| | | 100 | | | | | 105 | | | | | 110 | | | | |

| | | | | | | | | | | | | | | | | |
|---|---|---|---|---|---|---|---|---|---|---|---|---|---|---|---|---|
| ccg | ggt | gtt | ggc | gtg | ccg | ggc | gaa | ggc | gtg | ccg | ggt | gtt | ggt | gtt | ccg | 384 |
| Pro | Gly | Val | Gly | Val | Pro | Gly | Glu | Gly | Val | Pro | Gly | Val | Gly | Val | Pro | |
| | 115 | | | | | 120 | | | | | 125 | | | | | |

| | | | | | | | | | | | | | | | | |
|---|---|---|---|---|---|---|---|---|---|---|---|---|---|---|---|---|
| ggt | gta | ggg | gta | cca | ggt | gtt | ggt | gtt | ccg | ggt | gtt | ggc | gtg | ccg | ggc | 432 |
| Gly | Val | Gly | Val | Pro | Gly | Val | Gly | Val | Pro | Gly | Val | Gly | Val | Pro | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| gaa | ggc | gtg | ccg | ggt | gtt | ggt | gtt | ccg | ggt | gta | ggg | gta | cca | ggt | gtt | 480 |
| Glu | Gly | Val | Pro | Gly | Val | Gly | Val | Pro | Gly | Val | Gly | Val | Pro | Gly | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggt | gtt | ccg | ggt | gtt | ggc | gtg | ccg | ggc | gaa | ggc | gtg | ccg | ggt | gtt | ggt | 528 |
| Gly | Val | Pro | Gly | Val | Gly | Val | Pro | Gly | Glu | Gly | Val | Pro | Gly | Val | Gly | |
| | | | 165 | | | | | 170 | | | | | 175 | | | |

| | | | | | | | | | | | | | | | | |
|---|---|---|---|---|---|---|---|---|---|---|---|---|---|---|---|---|
| gtt | ccg | ggt | gta | ggg | gta | cca | ggt | gtt | ggt | gtt | ccg | ggt | gtt | ggc | gtg | 576 |
| Val | Pro | Gly | Val | Gly | Val | Pro | Gly | Val | Gly | Val | Pro | Gly | Val | Gly | Val | |
| | | 180 | | | | | 185 | | | | | 190 | | | | |

| | | | | | | | | | | | | | | | | |
|---|---|---|---|---|---|---|---|---|---|---|---|---|---|---|---|---|
| ccg | ggc | gaa | ggc | gtg | ccg | ggt | gtt | ggt | gtt | ccg | ggt | gta | ggg | gta | cca | 624 |
| Pro | Gly | Glu | Gly | Val | Pro | Gly | Val | Gly | Val | Pro | Gly | Val | Gly | Val | Pro | |
| | 195 | | | | | 200 | | | | | 205 | | | | | |

| | | | | | | | | | | | | | | | | |
|---|---|---|---|---|---|---|---|---|---|---|---|---|---|---|---|---|
| ggt | gtt | ggt | gtt | ccg | ggt | gtt | ggc | gtg | ccg | ggc | gaa | ggc | gtg | ccg | ggt | 672 |
| Gly | Val | Gly | Val | Pro | Gly | Val | Gly | Val | Pro | Gly | Glu | Gly | Val | Pro | Gly | |
| | 210 | | | | | 215 | | | | | 220 | | | | | |

```
gtt ggt gtt ccg ggt gta ggg gta cca ggt gtt ggt gtt ccg ggt gtt         720
Val Gly Val Pro Gly Val Gly Val Pro Gly Val Gly Val Pro Gly Val
225                 230                 235                 240 ggc gtg ccg ggc gaa ggc gtg ccg ggt gtt ggt gtt ccg ggt gta ggg         768
Gly Val Pro Gly Glu Gly Val Pro Gly Val Gly Val Pro Gly Val Gly
                245                 250                 255 gta ggt atc ccg ggc gtt ggt atc ccg ggc gtg ggt att ccg ggc gtt         816
Val Gly Ile Pro Gly Val Gly Ile Pro Gly Val Gly Ile Pro Gly Val
            260                 265                 270 ggt atc ccg ggc gta ggt atc cca ggc gtt ggt atc ccg ggc gtg ggt         864
Gly Ile Pro Gly Val Gly Ile Pro Gly Val Gly Ile Pro Gly Val Gly
        275                 280                 285 atc ccg ggc gtt ggt att ccg ggc gtg ggt atc ccg ggc gtt ggt atc         912
Ile Pro Gly Val Gly Ile Pro Gly Val Gly Ile Pro Gly Val Gly Ile
    290                 295                 300 cct ggt gta ggt atc ccg ggc gtt ggt atc ccg ggc gtg ggt att ccg         960
Pro Gly Val Gly Ile Pro Gly Val Gly Ile Pro Gly Val Gly Ile Pro
305                 310                 315                 320 ggc gtt ggt atc ccg ggc gta ggt atc cca ggc gtt ggt atc ccg ggc        1008
Gly Val Gly Ile Pro Gly Val Gly Ile Pro Gly Val Gly Ile Pro Gly
                325                 330                 335 gtg ggt atc ccg ggc gtt ggt att ccg ggc gtg ggt atc ccg ggc gtt        1056
Val Gly Ile Pro Gly Val Gly Ile Pro Gly Val Gly Ile Pro Gly Val
            340                 345                 350 ggt atc cct ggt gta ggt atc ccg ggc gtt ggt atc ccg ggc gtg ggt        1104
Gly Ile Pro Gly Val Gly Ile Pro Gly Val Gly Ile Pro Gly Val Gly
        355                 360                 365 att ccg ggc gtt ggt atc ccg ggc gta ggt atc cca ggc gtt ggt atc        1152
Ile Pro Gly Val Gly Ile Pro Gly Val Gly Ile Pro Gly Val Gly Ile
    370                 375                 380 ccg ggc gtg ggt atc ccg ggc gtt ggt att ccg ggc gtg ggt atc ccg        1200
Pro Gly Val Gly Ile Pro Gly Val Gly Ile Pro Gly Val Gly Ile Pro
385                 390                 395                 400 ggc gtt ggt atc cct ggt gta ggt atc ccg ggc gtt ggt atc ccg ggc        1248
Gly Val Gly Ile Pro Gly Val Gly Ile Pro Gly Val Gly Ile Pro Gly
                405                 410                 415 gtg ggt att ccg ggc gtt ggt atc ccg ggc gta ggt atc cca ggc gtt        1296
Val Gly Ile Pro Gly Val Gly Ile Pro Gly Val Gly Ile Pro Gly Val
            420                 425                 430 ggt atc ccg ggc gtg ggt atc ccg ggc gtt ggt att ccg ggc gtg ggt        1344
Gly Ile Pro Gly Val Gly Ile Pro Gly Val Gly Ile Pro Gly Val Gly
        435                 440                 445 atc ccg ggc gtt ggt atc cct ggt gta ggt atc ccg ggc gtt ggt atc        1392
Ile Pro Gly Val Gly Ile Pro Gly Val Gly Ile Pro Gly Val Gly Ile
    450                 455                 460 ccg ggc gtg ggt att ccg ggc gtt ggt atc ccg ggc gta ggt atc cca        1440
Pro Gly Val Gly Ile Pro Gly Val Gly Ile Pro Gly Val Gly Ile Pro
465                 470                 475                 480 ggc gtt ggt atc ccg ggc gtg ggt atc ccg ggc gtt ggt att ccg ggc        1488
Gly Val Gly Ile Pro Gly Val Gly Ile Pro Gly Val Gly Ile Pro Gly
                485                 490                 495 gtg ggt atc ccg ggc gtt ggt atc cct ggt gta ggt atc ccg ggc gtt        1536
Val Gly Ile Pro Gly Val Gly Ile Pro Gly Val Gly Ile Pro Gly Val
            500                 505                 510 ggt atc ccg ggc gtg ggt att ccg ggc gtt ggt atc ccg ggc gta ggt        1584
Gly Ile Pro Gly Val Gly Ile Pro Gly Val Gly Ile Pro Gly Val Gly
        515                 520                 525 atc cca ggc gtt ggt atc ccg ggc gtg ggt atc ccg ggc gtt ggt att        1632
Ile Pro Gly Val Gly Ile Pro Gly Val Gly Ile Pro Gly Val Gly Ile
    530                 535                 540
```

```
ccg ggc gtg ggt atc ccg ggc gtt ggt atc cct ggt gta cca ggt gtt      1680
Pro Gly Val Gly Ile Pro Gly Val Gly Ile Pro Gly Val Pro Gly Val
545                 550                 555                 560 ggt gtt ccg ggt gtt ggc gtg ccg ggc gaa ggc gtg ccg ggt gtt ggt      1728
Gly Val Pro Gly Val Gly Val Pro Gly Glu Gly Val Pro Gly Val Gly
                565                 570                 575 gtt ccg ggt gta ggg gta cca ggt gtt ggt gtt ccg ggt gtt ggc gtg      1776
Val Pro Gly Val Gly Val Pro Gly Val Gly Val Pro Gly Val Gly Val
            580                 585                 590 ccg ggc gaa ggc gtg ccg ggt gtt ggt gtt ccg ggt gta ggg gta cca      1824
Pro Gly Glu Gly Val Pro Gly Val Gly Val Pro Gly Val Gly Val Pro
        595                 600                 605 ggt gtt ggt gtt ccg ggt gtt ggc gtg ccg ggc gaa ggc gtg ccg ggt      1872
Gly Val Gly Val Pro Gly Val Gly Val Pro Gly Glu Gly Val Pro Gly
    610                 615                 620 gtt ggt gtt ccg ggt gta ggg gta cca ggt gtt ggt gtt ccg ggt gtt      1920
Val Gly Val Pro Gly Val Gly Val Pro Gly Val Gly Val Pro Gly Val
625                 630                 635                 640 ggc gtg ccg ggc gaa ggc gtg ccg ggt gtt ggt gtt ccg ggt gta ggg      1968
Gly Val Pro Gly Glu Gly Val Pro Gly Val Gly Val Pro Gly Val Gly
                645                 650                 655 gta cca ggt gtt ggt gtt ccg ggt gtt ggc gtg ccg ggc gaa ggc gtg      2016
Val Pro Gly Val Gly Val Pro Gly Val Gly Val Pro Gly Glu Gly Val
            660                 665                 670 ccg ggt gtt ggt gtt ccg ggt gta ggg gta cca ggt gtt ggt gtt ccg      2064
Pro Gly Val Gly Val Pro Gly Val Gly Val Pro Gly Val Gly Val Pro
        675                 680                 685 ggt gtt ggc gtg ccg ggc gaa ggc gtg ccg ggt gtt ggt gtt ccg ggt      2112
Gly Val Gly Val Pro Gly Glu Gly Val Pro Gly Val Gly Val Pro Gly
    690                 695                 700 gta ggg gta cca ggt gtt ggt gtt ccg ggt gtt ggc gtg ccg ggc gaa      2160
Val Gly Val Pro Gly Val Gly Val Pro Gly Val Gly Val Pro Gly Glu
705                 710                 715                 720 ggc gtg ccg ggt gtt ggt gtt ccg ggt gta ggg gta cca ggt gtt ggt      2208
Gly Val Pro Gly Val Gly Val Pro Gly Val Gly Val Pro Gly Val Gly
                725                 730                 735 gtt ccg ggt gtt ggc gtg ccg ggc gaa ggc gtg ccg ggt gtt ggt gtt      2256
Val Pro Gly Val Gly Val Pro Gly Glu Gly Val Pro Gly Val Gly Val
            740                 745                 750 ccg ggt gta ggg gta cca ggt gtt ggt gtt ccg ggt gtt ggc gtg ccg      2304
Pro Gly Val Gly Val Pro Gly Val Gly Val Pro Gly Val Gly Val Pro
        755                 760                 765 ggc gaa ggc gtg ccg ggt gtt ggt gtt ccg ggt gta ggg gta cca ggt      2352
Gly Glu Gly Val Pro Gly Val Gly Val Pro Gly Val Gly Val Pro Gly
    770                 775                 780 gtt ggt gtt ccg ggt gtt ggc gtg ccg ggc gaa ggc gtg ccg ggt gtt      2400
Val Gly Val Pro Gly Val Gly Val Pro Gly Glu Gly Val Pro Gly Val
785                 790                 795                 800 ggt gtt ccg ggt gta ggg gta ggt atc ccg ggc gtt ggt atc ccg ggc      2448
Gly Val Pro Gly Val Gly Val Gly Ile Pro Gly Val Gly Ile Pro Gly
                805                 810                 815 gtg ggt att ccg ggc gtt ggt atc ccg ggc gta ggt atc cca ggc gtt      2496
Val Gly Ile Pro Gly Val Gly Ile Pro Gly Val Gly Ile Pro Gly Val
            820                 825                 830 ggt atc ccg ggc gtg ggt atc ccg ggc gtt ggt att ccg ggc gtg ggt      2544
Gly Ile Pro Gly Val Gly Ile Pro Gly Val Gly Ile Pro Gly Val Gly
        835                 840                 845 atc ccg ggc gtt ggt atc cct ggt gta ggt atc ccg ggc gtt ggt atc      2592
Ile Pro Gly Val Gly Ile Pro Gly Val Gly Ile Pro Gly Val Gly Ile
    850                 855                 860
```

| | |
|---|---|
| ccg ggc gtg ggt att ccg ggc gtt ggt atc ccg ggc gta ggt atc cca<br>Pro Gly Val Gly Ile Pro Gly Val Gly Ile Pro Gly Val Gly Ile Pro<br>865                870              875              880 | 2640 |
| ggc gtt ggt atc ccg ggc gtg ggt atc ccg ggc gtt ggt att ccg ggc<br>Gly Val Gly Ile Pro Gly Val Gly Ile Pro Gly Val Gly Ile Pro Gly<br>             885               890               895 | 2688 |
| gtg ggt atc ccg ggc gtt ggt atc cct ggt gta ggt atc ccg ggc gtt<br>Val Gly Ile Pro Gly Val Gly Ile Pro Gly Val Gly Ile Pro Gly Val<br>900                905              910 | 2736 |
| ggt atc ccg ggc gtg ggt att ccg ggc gtt ggt atc ccg ggc gta ggt<br>Gly Ile Pro Gly Val Gly Ile Pro Gly Val Gly Ile Pro Gly Val Gly<br>             915               920               925 | 2784 |
| atc cca ggc gtt ggt atc ccg ggc gtg ggt atc ccg ggc gtt ggt att<br>Ile Pro Gly Val Gly Ile Pro Gly Val Gly Ile Pro Gly Val Gly Ile<br>930                935              940 | 2832 |
| ccg ggc gtg ggt atc ccg ggc gtt ggt atc cct ggt gta ggt atc ccg<br>Pro Gly Val Gly Ile Pro Gly Val Gly Ile Pro Gly Val Gly Ile Pro<br>945                950              955              960 | 2880 |
| ggc gtt ggt atc ccg ggc gtg ggt att ccg ggc gtt ggt atc ccg ggc<br>Gly Val Gly Ile Pro Gly Val Gly Ile Pro Gly Val Gly Ile Pro Gly<br>             965               970               975 | 2928 |
| gta ggt atc cca ggc gtt ggt atc ccg ggc gtg ggt atc ccg ggc gtt<br>Val Gly Ile Pro Gly Val Gly Ile Pro Gly Val Gly Ile Pro Gly Val<br>980                985              990 | 2976 |
| ggt att ccg ggc gtg ggt atc ccg  ggc gtt ggt atc cct  ggt gta ggt<br>Gly Ile Pro Gly Val Gly Ile Pro  Gly Val Gly Ile Pro  Gly Val Gly<br>             995               1000           1005 | 3024 |
| atc ccg  ggc gtt ggt atc ccg  ggc gtg ggt att ccg  ggc gtt ggt<br>Ile Pro  Gly Val Gly Ile Pro  Gly Val Gly Ile Pro  Gly Val Gly<br>1010               1015              1020 | 3069 |
| atc ccg  ggc gta ggt atc cca  ggc gtt ggt atc ccg  ggc gtg ggt<br>Ile Pro  Gly Val Gly Ile Pro  Gly Val Gly Ile Pro  Gly Val Gly<br>1025               1030              1035 | 3114 |
| atc ccg  ggc gtt ggt att ccg  ggc gtg ggt atc ccg  ggc gtt ggt<br>Ile Pro  Gly Val Gly Ile Pro  Gly Val Gly Ile Pro  Gly Val Gly<br>1040               1045              1050 | 3159 |
| atc cct  ggt gta ggt atc ccg  ggc gtt ggt atc ccg  ggc gtg ggt<br>Ile Pro  Gly Val Gly Ile Pro  Gly Val Gly Ile Pro  Gly Val Gly<br>1055               1060              1065 | 3204 |
| att ccg  ggc gtt ggt atc ccg  ggc gta ggt atc cca  ggc gtt ggt<br>Ile Pro  Gly Val Gly Ile Pro  Gly Val Gly Ile Pro  Gly Val Gly<br>1070               1075              1080 | 3249 |
| atc ccg  ggc gtg ggt atc ccg  ggc gtt ggt att ccg  ggc gtg ggt<br>Ile Pro  Gly Val Gly Ile Pro  Gly Val Gly Ile Pro  Gly Val Gly<br>1085               1090              1095 | 3294 |
| atc ccg  ggc gtt ggt atc cct  ggt gta ccg ggc atc  ggt gtt ccg<br>Ile Pro  Gly Val Gly Ile Pro  Gly Val Pro Gly Ile  Gly Val Pro<br>1100               1105              1110 | 3339 |
| ggc att  ggt gtg ccg ggc atc  ggt gtt ccg ggc att  ggt gtg ccg<br>Gly Ile  Gly Val Pro Gly Ile  Gly Val Pro Gly Ile  Gly Val Pro<br>1115               1120              1125 | 3384 |
| ggc atc  ggt gtg cca ggc att  ggt gtg ccg ggc atc  ggt gtt ccg<br>Gly Ile  Gly Val Pro Gly Ile  Gly Val Pro Gly Ile  Gly Val Pro<br>1130               1135              1140 | 3429 |
| ggc att  ggt gtg ccg ggc atc  ggt gtg cca ggc att  ggt gca gta<br>Gly Ile  Gly Val Pro Gly Ile  Gly Val Pro Gly Ile  Gly Ala Val<br>1145               1150              1155 | 3474 |
| acc ggt  cgt ggg gat tct cct  gcg tcc agc gtc ccg  ggc atc ggt<br>Thr Gly  Arg Gly Asp Ser Pro  Ala Ser Ser Val Pro  Gly Ile Gly<br>1160               1165              1170 | 3519 |

```
gtt ccg ggc att ggt gtg ccg ggc atc ggt gtt ccg ggc att ggt      3564
Val Pro Gly Ile Gly Val Pro Gly Ile Gly Val Pro Gly Ile Gly
    1175                1180                1185 gtg ccg ggc atc ggt gtg cca ggc att ggt gtg ccg ggc atc ggt      3609
Val Pro Gly Ile Gly Val Pro Gly Ile Gly Val Pro Gly Ile Gly
    1190                1195                1200 gtt ccg ggc att ggt gtg cca ggc atc ggt gtg ccg ggc att ggt      3654
Val Pro Gly Ile Gly Val Pro Gly Ile Gly Val Pro Gly Ile Gly
    1205                1210                1215 gta ccg ggc atc ggt gtt ccg ggc att ggt gtg ccg ggc atc ggt      3699
Val Pro Gly Ile Gly Val Pro Gly Ile Gly Val Pro Gly Ile Gly
    1220                1225                1230 gtt ccg ggc att ggt gtg ccg ggc atc ggt gtg cca ggc att ggt      3744
Val Pro Gly Ile Gly Val Pro Gly Ile Gly Val Pro Gly Ile Gly
    1235                1240                1245 gtg ccg ggc atc ggt gtt ccg ggc att ggt gtg ccg ggc atc ggt      3789
Val Pro Gly Ile Gly Val Pro Gly Ile Gly Val Pro Gly Ile Gly
    1250                1255                1260 gtg cca ggc att ggt gca gta acc ggt cgt ggg gat tct cct gcg      3834
Val Pro Gly Ile Gly Ala Val Thr Gly Arg Gly Asp Ser Pro Ala
    1265                1270                1275 tcc agc gtc ccg ggc atc ggt gtt ccg ggc att ggt gtg ccg ggc      3879
Ser Ser Val Pro Gly Ile Gly Val Pro Gly Ile Gly Val Pro Gly
    1280                1285                1290 atc ggt gtt ccg ggc att ggt gtg ccg ggc atc ggt gtg cca ggc      3924
Ile Gly Val Pro Gly Ile Gly Val Pro Gly Ile Gly Val Pro Gly
    1295                1300                1305 att ggt gtg ccg ggc atc ggt gtt ccg ggc att ggt gtg cca ggc      3969
Ile Gly Val Pro Gly Ile Gly Val Pro Gly Ile Gly Val Pro Gly
    1310                1315                1320 atc ggt gtg ccg ggc att ggt gta tga                              3996
Ile Gly Val Pro Gly Ile Gly Val
    1325                1330

<210> SEQ ID NO 22
<211> LENGTH: 1331
<212> TYPE: PRT
<213> ORGANISM: Artificial Sequence
<220> FEATURE:
<223> OTHER INFORMATION: Synthetic Construct

<400> SEQUENCE: 22

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Gly Val
                20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
            100                 105                 110

Pro Gly Val Gly Val Pro Gly Glu Gly Val Pro Gly Val Gly Val Pro
        115                 120                 125

Gly Val Gly Val Pro Gly Val Gly Val Pro Gly Val Gly Val Pro Gly
    130                 135                 140
```

-continued

```
Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
        195                 200                 205

Gly Val Gly Val Pro Gly Val Gly Val Pro Gly Glu Gly Val Pro Gly
210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Gly Ile Pro Gly Val Gly Ile Pro Gly Val Gly Ile Pro Gly Val
            260                 265                 270

Gly Ile Pro Gly Val Gly Ile Pro Gly Val Gly Ile Pro Gly Val Gly
        275                 280                 285

Ile Pro Gly Val Gly Ile Pro Gly Val Gly Ile Pro Gly Val Gly Ile
290                 295                 300

Pro Gly Val Gly Ile Pro Gly Val Gly Ile Pro Gly Val Gly Ile Pro
305                 310                 315                 320

Gly Val Gly Ile Pro Gly Val Gly Ile Pro Gly Val Gly Ile Pro Gly
                325                 330                 335

Val Gly Ile Pro Gly Val Gly Ile Pro Gly Val Gly Ile Pro Gly Val
            340                 345                 350

Gly Ile Pro Gly Val Gly Ile Pro Gly Val Gly Ile Pro Gly Val Gly
        355                 360                 365

Ile Pro Gly Val Gly Ile Pro Gly Val Gly Ile Pro Gly Val Gly Ile
370                 375                 380

Pro Gly Val Gly Ile Pro Gly Val Gly Ile Pro Gly Val Gly Ile Pro
385                 390                 395                 400

Gly Val Gly Ile Pro Gly Val Gly Ile Pro Gly Val Gly Ile Pro Gly
                405                 410                 415

Val Gly Ile Pro Gly Val Gly Ile Pro Gly Val Gly Ile Pro Gly Val
            420                 425                 430

Gly Ile Pro Gly Val Gly Ile Pro Gly Val Gly Ile Pro Gly Val Gly
        435                 440                 445

Ile Pro Gly Val Gly Ile Pro Gly Val Gly Ile Pro Gly Val Gly Ile
450                 455                 460

Pro Gly Val Gly Ile Pro Gly Val Gly Ile Pro Gly Val Gly Ile Pro
465                 470                 475                 480

Gly Val Gly Ile Pro Gly Val Gly Ile Pro Gly Val Gly Ile Pro Gly
                485                 490                 495

Val Gly Ile Pro Gly Val Gly Ile Pro Gly Val Gly Ile Pro Gly Val
            500                 505                 510

Gly Ile Pro Gly Val Gly Ile Pro Gly Val Gly Ile Pro Gly Val Gly
        515                 520                 525

Ile Pro Gly Val Gly Ile Pro Gly Val Gly Ile Pro Gly Val Gly Ile
530                 535                 540

Pro Gly Val Gly Ile Pro Gly Val Gly Ile Pro Gly Val Pro Gly Val
545                 550                 555                 560
```

-continued

Gly Val Pro Gly Val Gly Val Pro Gly Glu Gly Val Pro Gly Val Gly
            565                 570                 575
Val Pro Gly Val Gly Val Pro Gly Val Gly Val Pro Gly Val Gly Val
            580                 585                 590
Pro Gly Glu Gly Val Pro Gly Val Gly Val Pro Gly Val Gly Val Pro
            595                 600                 605
Gly Val Gly Val Pro Gly Val Gly Val Pro Gly Glu Gly Val Pro Gly
            610                 615                 620
Val Gly Val Pro Gly Val Gly Val Pro Gly Val Gly Val Pro Gly Val
625                 630                 635                 640
Gly Val Pro Gly Glu Gly Val Pro Gly Val Gly Val Pro Gly Val Gly
            645                 650                 655
Val Pro Gly Val Gly Val Pro Gly Val Gly Val Pro Gly Glu Gly Val
            660                 665                 670
Pro Gly Val Gly Val Pro Gly Val Gly Val Pro Gly Val Gly Val Pro
            675                 680                 685
Gly Val Gly Val Pro Gly Glu Gly Val Pro Gly Val Gly Val Pro Gly
            690                 695                 700
Val Gly Val Pro Gly Val Gly Val Pro Gly Val Gly Val Pro Gly Glu
705                 710                 715                 720
Gly Val Pro Gly Val Gly Val Pro Gly Val Gly Val Pro Gly Val Gly
            725                 730                 735
Val Pro Gly Val Gly Val Pro Gly Glu Gly Val Pro Gly Val Gly Val
            740                 745                 750
Pro Gly Val Gly Val Pro Gly Val Gly Val Pro Gly Val Gly Val Pro
            755                 760                 765
Gly Glu Gly Val Pro Gly Val Gly Val Pro Gly Val Gly Val Pro Gly
            770                 775                 780
Val Gly Val Pro Gly Val Gly Val Pro Gly Glu Gly Val Pro Gly Val
785                 790                 795                 800
Gly Val Pro Gly Val Gly Val Gly Ile Pro Gly Val Gly Ile Pro Gly
            805                 810                 815
Val Gly Ile Pro Gly Val Gly Ile Pro Gly Val Gly Ile Pro Gly Val
            820                 825                 830
Gly Ile Pro Gly Val Gly Ile Pro Gly Val Gly Ile Pro Gly Val Gly
            835                 840                 845
Ile Pro Gly Val Gly Ile Pro Gly Val Gly Ile Pro Gly Val Gly Ile
            850                 855                 860
Pro Gly Val Gly Ile Pro Gly Val Gly Ile Pro Gly Val Gly Ile Pro
865                 870                 875                 880
Gly Val Gly Ile Pro Gly Val Gly Ile Pro Gly Val Gly Ile Pro Gly
            885                 890                 895
Val Gly Ile Pro Gly Val Gly Ile Pro Gly Val Gly Ile Pro Gly Val
            900                 905                 910
Gly Ile Pro Gly Val Gly Ile Pro Gly Val Gly Ile Pro Gly Val Gly
            915                 920                 925
Ile Pro Gly Val Gly Ile Pro Gly Val Gly Ile Pro Gly Val Gly Ile
            930                 935                 940
Pro Gly Val Gly Ile Pro Gly Val Gly Ile Pro Gly Val Gly Ile Pro
945                 950                 955                 960
Gly Val Gly Ile Pro Gly Val Gly Ile Pro Gly Val Gly Ile Pro Gly
            965                 970                 975
Val Gly Ile Pro Gly Val Gly Ile Pro Gly Val Gly Ile Pro Gly Val
            980                 985                 990

-continued

```
Gly Ile Pro Gly Val Gly Ile Pro  Gly Val Gly Ile Pro  Gly Val Gly
        995                 1000                 1005

Ile Pro Gly Val Gly Ile Pro  Gly Val Gly Ile Pro  Gly Val Gly
    1010                 1015                 1020

Ile Pro Gly Val Gly Ile Pro  Gly Val Gly Ile Pro  Gly Val Gly
    1025                 1030                 1035

Ile Pro Gly Val Gly Ile Pro  Gly Val Gly Ile Pro  Gly Val Gly
    1040                 1045                 1050

Ile Pro Gly Val Gly Ile Pro  Gly Val Gly Ile Pro  Gly Val Gly
    1055                 1060                 1065

Ile Pro Gly Val Gly Ile Pro  Gly Val Gly Ile Pro  Gly Val Gly
    1070                 1075                 1080

Ile Pro Gly Val Gly Ile Pro  Gly Val Gly Ile Pro  Gly Val Gly
    1085                 1090                 1095

Ile Pro Gly Val Gly Ile Pro  Gly Val Pro Gly Ile  Gly Val Pro
    1100                 1105                 1110

Gly Ile Gly Val Pro Gly Ile  Gly Val Pro Gly Ile  Gly Val Pro
    1115                 1120                 1125

Gly Ile Gly Val Pro Gly Ile  Gly Val Pro Gly Ile  Gly Val Pro
    1130                 1135                 1140

Gly Ile Gly Val Pro Gly Ile  Gly Val Pro Gly Ile  Gly Ala Val
    1145                 1150                 1155

Thr Gly Arg Gly Asp Ser Pro  Ala Ser Ser Val Pro  Gly Ile Gly
    1160                 1165                 1170

Val Pro Gly Ile Gly Val Pro  Gly Ile Gly Val Pro  Gly Ile Gly
    1175                 1180                 1185

Val Pro Gly Ile Gly Val Pro  Gly Ile Gly Val Pro  Gly Ile Gly
    1190                 1195                 1200

Val Pro Gly Ile Gly Val Pro  Gly Ile Gly Val Pro  Gly Ile Gly
    1205                 1210                 1215

Val Pro Gly Ile Gly Val Pro  Gly Ile Gly Val Pro  Gly Ile Gly
    1220                 1225                 1230

Val Pro Gly Ile Gly Val Pro  Gly Ile Gly Val Pro  Gly Ile Gly
    1235                 1240                 1245

Val Pro Gly Ile Gly Val Pro  Gly Ile Gly Val Pro  Gly Ile Gly
    1250                 1255                 1260

Val Pro Gly Ile Gly Ala Val  Thr Gly Arg Gly Asp  Ser Pro Ala
    1265                 1270                 1275

Ser Ser Val Pro Gly Ile Gly  Val Pro Gly Ile Gly  Val Pro Gly
    1280                 1285                 1290

Ile Gly Val Pro Gly Ile Gly  Val Pro Gly Ile Gly  Val Pro Gly
    1295                 1300                 1305

Ile Gly Val Pro Gly Ile Gly  Val Pro Gly Ile Gly  Val Pro Gly
    1310                 1315                 1320

Ile Gly Val Pro Gly Ile Gly  Val
    1325                 1330

<210> SEQ ID NO 23
<211> LENGTH: 300
<212> TYPE: DNA
<213> ORGANISM: Artificial Sequence
<220> FEATURE:
<223> OTHER INFORMATION: Synthetic construct of Sequence for B20 of
      biopolymer B

<400> SEQUENCE: 23
```

-continued

```
gtaccggccg tgggcgttcc agcagtgggt gttccggctg tgggcgttcc ggcggtgggt      60
gttccggcgg tgggcgttcc ggctgtgggt gttccggcgg tgggcgttcc tgcggtgggt     120
gttccagcag tgggtgttcc tgccgtcggg gtcccggccg tcggtgttcc agcagtgggc     180
gttcctgcgg tgggtgttcc ggcggtgggc gttccggcgg tgggtgttcc ggcggtgggc     240
gttccggcgg tgggtgttcc ggctgtgggc gttccagccg tgggtgttcc ggcagtgggc     300
```

<210> SEQ ID NO 24
<211> LENGTH: 2796
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(2796)

<400> SEQUENCE: 24

```
atg gaa tcc ctg ctg ccg gta cca ggt gtt ggt gtt ccg ggt gtt ggc      48
Met Glu Ser Leu Leu Pro Val Pro Gly Val Gly Val Pro Gly Val Gly
1               5                   10                  15 gtg ccg ggc gaa ggc gtg ccg ggt gtt ggt gtt ccg ggt gta ggg gta      96
Val Pro Gly Glu Gly Val Pro Gly Val Gly Val Pro Gly Val Gly Val
                20                  25                  30 cca ggt gtt ggt gtt ccg ggt ggc gtg ccg ggc gaa ggc gtg ccg          144
Pro Gly Val Gly Val Pro Gly Gly Val Pro Gly Glu Gly Val Pro
            35                  40                  45 ggt gtt ggt gtt ccg ggt gta ggg gta cca ggt gtt ggt gtt ccg ggt      192
Gly Val Gly Val Pro Gly Val Gly Val Pro Gly Val Gly Val Pro Gly
        50                  55                  60 gtt ggc gtg ccg ggc gaa ggc gtg ccg ggt gtt ggt gtt ccg ggt gta      240
Val Gly Val Pro Gly Glu Gly Val Pro Gly Val Gly Val Pro Gly Val
65                  70                  75                  80 ggg gta cca ggt gtt ggt gtt ccg ggt gtt ggc gtg ccg ggc gaa ggc      288
Gly Val Pro Gly Val Gly Val Pro Gly Val Gly Val Pro Gly Glu Gly
                85                  90                  95 gtg ccg ggt gtt ggt gtt ccg ggt gta ggg gta cca ggt gtt ggt gtt      336
Val Pro Gly Val Gly Val Pro Gly Val Gly Val Pro Gly Val Gly Val
                100                 105                 110 ccg ggt gtt ggc gtg ccg ggc gaa ggc gtg ccg ggt gtt ggt gtt ccg      384
Pro Gly Val Gly Val Pro Gly Glu Gly Val Pro Gly Val Gly Val Pro
            115                 120                 125 ggt gta ggg gta cca ggt gtt ggt gtt ccg ggt gtt ggc gtg ccg ggc      432
Gly Val Gly Val Pro Gly Val Gly Val Pro Gly Val Gly Val Pro Gly
        130                 135                 140 gaa ggc gtg ccg ggt gtt ggt gtt ccg ggt gta ggg gta cca ggt gtt      480
Glu Gly Val Pro Gly Val Gly Val Pro Gly Val Gly Val Pro Gly Val
145                 150                 155                 160 ggt gtt ccg ggt gtt ggc gtg ccg ggc gaa ggc gtg ccg ggt gtt ggt      528
Gly Val Pro Gly Val Gly Val Pro Gly Glu Gly Val Pro Gly Val Gly
                165                 170                 175 gtt ccg ggt gta ggg gta cca ggt gtt ggt gtt ccg ggt gtt ggc gtg      576
Val Pro Gly Val Gly Val Pro Gly Val Gly Val Pro Gly Val Gly Val
                180                 185                 190 ccg ggc gaa ggc gtg ccg ggt gtt ggt gtt ccg ggt gta ggg gta cca      624
Pro Gly Glu Gly Val Pro Gly Val Gly Val Pro Gly Val Gly Val Pro
            195                 200                 205 ggt gtt ggt gtt ccg ggt gtt ggc gtg ccg ggc gaa ggc gtg ccg ggt      672
Gly Val Gly Val Pro Gly Val Gly Val Pro Gly Glu Gly Val Pro Gly
        210                 215                 220
```

| | | |
|---|---|---|
| gtt ggt gtt ccg ggt gta ggg gta cca ggt gtt ggt gtt ccg ggt gtt | 720 | |
| Val Gly Val Pro Gly Val Gly Val Pro Gly Val Gly Val Pro Gly Val | | |
| 225 230 235 240 | | |
| ggc gtg ccg ggc gaa ggc gtg ccg ggt gtt ggt gtt ccg ggt gta ggg | 768 | |
| Gly Val Pro Gly Glu Gly Val Pro Gly Val Gly Val Pro Gly Val Gly | | |
| 245 250 255 | | |
| gta ccg gcc gtg ggc gtt cca gca gtg ggt gtt ccg gct gtg ggc gtt | 816 | |
| Val Pro Ala Val Gly Val Pro Ala Val Gly Val Pro Ala Val Gly Val | | |
| 260 265 270 | | |
| ccg gcg gtg ggt gtt ccg gcg gtg ggc gtt ccg gct gtg ggt gtt ccg | 864 | |
| Pro Ala Val Gly Val Pro Ala Val Gly Val Pro Ala Val Gly Val Pro | | |
| 275 280 285 | | |
| gcg gtg ggc gtt cct gcg gtg ggt gtt cca gca gtg ggt gtt cct gcc | 912 | |
| Ala Val Gly Val Pro Ala Val Gly Val Pro Ala Val Gly Val Pro Ala | | |
| 290 295 300 | | |
| gtc ggg gtc ccg gcc gtc ggt gtt cca gca gtg ggc gtt cct gcg gtg | 960 | |
| Val Gly Val Pro Ala Val Gly Val Pro Ala Val Gly Val Pro Ala Val | | |
| 305 310 315 320 | | |
| ggt gtt ccg gcg gtg ggc gtt ccg gcg gtg ggt gtt ccg gcg gtg ggc | 1008 | |
| Gly Val Pro Ala Val Gly Val Pro Ala Val Gly Val Pro Ala Val Gly | | |
| 325 330 335 | | |
| gtt ccg gcg gtg ggt gtt ccg gct gtg ggc gtt cca gcc gtg ggt gtt | 1056 | |
| Val Pro Ala Val Gly Val Pro Ala Val Gly Val Pro Ala Val Gly Val | | |
| 340 345 350 | | |
| ccg gca gtg ggc gta cca ggt gtt ggt gtt ccg ggt gtt ggc gtg ccg | 1104 | |
| Pro Ala Val Gly Val Pro Gly Val Gly Val Pro Gly Val Gly Val Pro | | |
| 355 360 365 | | |
| ggc gaa ggc gtg ccg ggt gtt ggt gtt ccg ggt gta ggg gta cca ggt | 1152 | |
| Gly Glu Gly Val Pro Gly Val Gly Val Pro Gly Val Gly Val Pro Gly | | |
| 370 375 380 | | |
| gtt ggt gtt ccg ggt gtt ggc gtg ccg ggc gaa ggc gtg ccg ggt gtt | 1200 | |
| Val Gly Val Pro Gly Val Gly Val Pro Gly Glu Gly Val Pro Gly Val | | |
| 385 390 395 400 | | |
| ggt gtt ccg ggt gta ggg gta cca ggt gtt ggt gtt ccg ggt gtt ggc | 1248 | |
| Gly Val Pro Gly Val Gly Val Pro Gly Val Gly Val Pro Gly Val Gly | | |
| 405 410 415 | | |
| gtg ccg ggc gaa ggc gtg ccg ggt gtt ggt gtt ccg ggt gta ggg gta | 1296 | |
| Val Pro Gly Glu Gly Val Pro Gly Val Gly Val Pro Gly Val Gly Val | | |
| 420 425 430 | | |
| cca ggt gtt ggt gtt ccg ggt gtt ggc gtg ccg ggc gaa ggc gtg ccg | 1344 | |
| Pro Gly Val Gly Val Pro Gly Val Gly Val Pro Gly Glu Gly Val Pro | | |
| 435 440 445 | | |
| ggt gtt ggt gtt ccg ggt gta ggg gta cca ggt gtt ggt gtt ccg ggt | 1392 | |
| Gly Val Gly Val Pro Gly Val Gly Val Pro Gly Val Gly Val Pro Gly | | |
| 450 455 460 | | |
| gtt ggc gtg ccg ggc gaa ggc gtg ccg ggt gtt ggt gtt ccg ggt gta | 1440 | |
| Val Gly Val Pro Gly Glu Gly Val Pro Gly Val Gly Val Pro Gly Val | | |
| 465 470 475 480 | | |
| ggg gta cca ggt gtt ggt gtt ccg ggt gtt ggc gtg ccg ggc gaa ggc | 1488 | |
| Gly Val Pro Gly Val Gly Val Pro Gly Val Gly Val Pro Gly Glu Gly | | |
| 485 490 495 | | |
| gtg ccg ggt gtt ggt gtt ccg ggt gta ggg gta cca ggt gtt ggt gtt | 1536 | |
| Val Pro Gly Val Gly Val Pro Gly Val Gly Val Pro Gly Val Gly Val | | |
| 500 505 510 | | |
| ccg ggt gtt ggc gtg ccg ggc gaa ggc gtg ccg ggt gtt ggt gtt ccg | 1584 | |
| Pro Gly Val Gly Val Pro Gly Glu Gly Val Pro Gly Val Gly Val Pro | | |
| 515 520 525 | | |
| ggt gta ggg gta cca ggt gtt ggt gtt ccg ggt gtt ggc gtg ccg ggc | 1632 | |
| Gly Val Gly Val Pro Gly Val Gly Val Pro Gly Val Gly Val Pro Gly | | |
| 530 535 540 | | |

```
gaa ggc gtg ccg ggt gtt ggt gtt ccg ggt gta ggg gta cca ggt gtt      1680
Glu Gly Val Pro Gly Val Gly Val Pro Gly Val Gly Val Pro Gly Val
545                 550                 555                 560 ggt gtt ccg ggt gtt ggc gtg ccg ggc gaa ggc gtg ccg ggt gtt ggt      1728
Gly Val Pro Gly Val Gly Val Pro Gly Glu Gly Val Pro Gly Val Gly
                565                 570                 575 gtt ccg ggt gta ggg gta cca ggt gtt ggt gtt ccg ggt gtt ggc gtg      1776
Val Pro Gly Val Gly Val Pro Gly Val Gly Val Pro Gly Val Gly Val
            580                 585                 590 ccg ggc gaa ggc gtg ccg ggt gtt ggt gtt ccg ggt gta ggg gta ccg      1824
Pro Gly Glu Gly Val Pro Gly Val Gly Val Pro Gly Val Gly Val Pro
        595                 600                 605 gcc gtg ggc gtt cca gca gtg ggt gtt ccg gct gtg ggc gtt ccg gcg      1872
Ala Val Gly Val Pro Ala Val Gly Val Pro Ala Val Gly Val Pro Ala
610                 615                 620 gtg ggt gtt ccg gcg gtg ggc gtt ccg gct gtg ggt gtt ccg gcg gtg      1920
Val Gly Val Pro Ala Val Gly Val Pro Ala Val Gly Val Pro Ala Val
625                 630                 635                 640 ggc gtt cct gcg gtg ggt gtt cca gca gtg ggt gtt cct gcc gtc ggg      1968
Gly Val Pro Ala Val Gly Val Pro Ala Val Gly Val Pro Ala Val Gly
                645                 650                 655 gtc ccg gcc gtc ggt gtt cca gca gtg ggc gtt cct gcg gtg ggt gtt      2016
Val Pro Ala Val Gly Val Pro Ala Val Gly Val Pro Ala Val Gly Val
            660                 665                 670 ccg gcg gtg ggc gtt ccg gcg gtg ggt gtt ccg gcg gtg ggc gtt ccg      2064
Pro Ala Val Gly Val Pro Ala Val Gly Val Pro Ala Val Gly Val Pro
        675                 680                 685 gcg gtg ggt gtt ccg gct gtg ggc gtt cca gcc gtg ggt gtt ccg gca      2112
Ala Val Gly Val Pro Ala Val Gly Val Pro Ala Val Gly Val Pro Ala
690                 695                 700 gtg ggc gta ccg ggc atc ggt gtt ccg ggc att ggt gtg ccg ggc atc      2160
Val Gly Val Pro Gly Ile Gly Val Pro Gly Ile Gly Val Pro Gly Ile
705                 710                 715                 720 ggt gtt ccg ggc att ggt gtg ccg ggc atc ggt gtg cca ggc att ggt      2208
Gly Val Pro Gly Ile Gly Val Pro Gly Ile Gly Val Pro Gly Ile Gly
                725                 730                 735 gtg ccg ggc atc ggt gtt ccg ggc att ggt gtg ccg ggc atc ggt gtg      2256
Val Pro Gly Ile Gly Val Pro Gly Ile Gly Val Pro Gly Ile Gly Val
            740                 745                 750 cca ggc att ggt gca gta acc ggt cgt ggg gat tct cct gcg tcc agc      2304
Pro Gly Ile Gly Ala Val Thr Gly Arg Gly Asp Ser Pro Ala Ser Ser
        755                 760                 765 gtc ccg ggc atc ggt gtt ccg ggc att ggt gtg ccg ggc atc ggt gtt      2352
Val Pro Gly Ile Gly Val Pro Gly Ile Gly Val Pro Gly Ile Gly Val
770                 775                 780 ccg ggc att ggt gtg ccg ggc atc ggt gtg cca ggc att ggt gtg ccg      2400
Pro Gly Ile Gly Val Pro Gly Ile Gly Val Pro Gly Ile Gly Val Pro
785                 790                 795                 800 ggc atc ggt gtt ccg ggc att ggt gtg cca ggc atc ggt gtg ccg ggc      2448
Gly Ile Gly Val Pro Gly Ile Gly Val Pro Gly Ile Gly Val Pro Gly
                805                 810                 815 att ggt gta ccg ggc atc ggt gtt ccg ggc att ggt gtg ccg ggc atc      2496
Ile Gly Val Pro Gly Ile Gly Val Pro Gly Ile Gly Val Pro Gly Ile
            820                 825                 830 ggt gtt ccg ggc att ggt gtg ccg ggc atc ggt gtg cca ggc att ggt      2544
Gly Val Pro Gly Ile Gly Val Pro Gly Ile Gly Val Pro Gly Ile Gly
        835                 840                 845 gtg ccg ggc atc ggt gtt ccg ggc att ggt gtg ccg ggc atc ggt gtg      2592
Val Pro Gly Ile Gly Val Pro Gly Ile Gly Val Pro Gly Ile Gly Val
850                 855                 860
```

```
cca ggc att ggt gca gta acc ggt cgt ggg gat tct cct gcg tcc agc    2640
Pro Gly Ile Gly Ala Val Thr Gly Arg Gly Asp Ser Pro Ala Ser Ser
865                 870                 875                 880 gtc ccg ggc atc ggt gtt ccg ggc att ggt gtg ccg ggc atc ggt gtt    2688
Val Pro Gly Ile Gly Val Pro Gly Ile Gly Val Pro Gly Ile Gly Val
                885                 890                 895 ccg ggc att ggt gtg ccg ggc atc ggt gtg cca ggc att ggt gtg ccg    2736
Pro Gly Ile Gly Val Pro Gly Ile Gly Val Pro Gly Ile Gly Val Pro
            900                 905                 910 ggc atc ggt gtt ccg ggc att ggt gtg cca ggc atc ggt gtg ccg ggc    2784
Gly Ile Gly Val Pro Gly Ile Gly Val Pro Gly Ile Gly Val Pro Gly
        915                 920                 925 att ggt gta tga                                                    2796
Ile Gly Val
    930

<210> SEQ ID NO 25
<211> LENGTH: 931
<212> TYPE: PRT
<213> ORGANISM: Artificial Sequence
<220> FEATURE:
<223> OTHER INFORMATION: Synthetic construct

<400> SEQUENCE: 25

Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
                20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
            100                 105                 110

Pro Gly Val Gly Val Pro Gly Glu Gly Val Pro Gly Val Gly Val Pro
        115                 120                 125

Gly Val Gly Val Pro Gly Val Gly Val Pro Gly Val Gly Val Pro Gly
    130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
            180                 185                 190

Pro Gly Glu Gly Val Pro Gly Val Gly Val Pro Gly Val Gly Val Pro
        195                 200                 205

Gly Val Gly Val Pro Gly Val Gly Val Pro Gly Glu Gly Val Pro Gly
    210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Pro Ala Val Gly Val Pro Ala Val Gly Val Pro Ala Val Gly Val
            260                 265                 270
```

-continued

Pro Ala Gly Val Pro Ala Val Gly Val Pro Ala Val Gly Val Pro
        275                 280                 285
Ala Val Gly Val Pro Ala Val Gly Val Pro Ala Val Gly Val Pro Ala
        290                 295                 300
Val Gly Val Pro Ala Val Gly Val Pro Ala Val Gly Val Pro Ala Val
305                 310                 315                 320
Gly Val Pro Ala Val Gly Val Pro Ala Val Gly Val Pro Ala Val Gly
        325                 330                 335
Val Pro Ala Val Gly Val Pro Ala Val Gly Val Pro Ala Val Gly Val
        340                 345                 350
Pro Ala Val Gly Val Pro Gly Val Gly Val Pro Gly Val Gly Val Pro
        355                 360                 365
Gly Glu Gly Val Pro Gly Val Gly Val Pro Gly Val Gly Val Pro Gly
        370                 375                 380
Val Gly Val Pro Gly Val Gly Val Pro Gly Glu Gly Val Pro Gly Val
385                 390                 395                 400
Gly Val Pro Gly Val Gly Val Pro Gly Val Gly Val Pro Gly Val Gly
        405                 410                 415
Val Pro Gly Glu Gly Val Pro Gly Val Gly Val Pro Gly Val Gly Val
        420                 425                 430
Pro Gly Val Gly Val Pro Gly Val Gly Val Pro Gly Glu Gly Val Pro
        435                 440                 445
Gly Val Gly Val Pro Gly Val Gly Val Pro Gly Val Gly Val Pro Gly
        450                 455                 460
Val Gly Val Pro Gly Glu Gly Val Pro Gly Val Gly Val Pro Gly Val
465                 470                 475                 480
Gly Val Pro Gly Val Gly Val Pro Gly Val Gly Val Pro Gly Glu Gly
        485                 490                 495
Val Pro Gly Val Gly Val Pro Gly Val Gly Val Pro Gly Val Gly Val
        500                 505                 510
Pro Gly Val Gly Val Pro Gly Glu Gly Val Pro Gly Val Gly Val Pro
        515                 520                 525
Gly Val Gly Val Pro Gly Val Gly Val Pro Gly Val Gly Val Pro Gly
        530                 535                 540
Glu Gly Val Pro Gly Val Gly Val Pro Gly Val Gly Val Pro Gly Val
545                 550                 555                 560
Gly Val Pro Gly Val Gly Val Pro Gly Glu Gly Val Pro Gly Val Gly
        565                 570                 575
Val Pro Gly Val Gly Val Pro Gly Val Gly Val Pro Gly Val Gly Val
        580                 585                 590
Pro Gly Glu Gly Val Pro Gly Val Gly Val Pro Gly Val Gly Val Pro
        595                 600                 605
Ala Val Gly Val Pro Ala Val Gly Val Pro Ala Val Gly Val Pro Ala
        610                 615                 620
Val Gly Val Pro Ala Val Gly Val Pro Ala Val Gly Val Pro Ala Val
625                 630                 635                 640
Gly Val Pro Ala Val Gly Val Pro Ala Val Gly Val Pro Ala Val Gly
        645                 650                 655
Val Pro Ala Val Gly Val Pro Ala Val Gly Val Pro Ala Val Gly Val
        660                 665                 670
Pro Ala Val Gly Val Pro Ala Val Gly Val Pro Ala Val Gly Val Pro
        675                 680                 685

```
Ala Val Gly Val Pro Ala Val Gly Val Pro Ala Val Gly Val Pro Ala
    690                 695                 700
Val Gly Val Pro Gly Ile Gly Val Pro Gly Ile Gly Val Pro Gly Ile
705                 710                 715                 720
Gly Val Pro Gly Ile Gly Val Pro Gly Ile Gly Val Pro Gly Ile Gly
                725                 730                 735
Val Pro Gly Ile Gly Val Pro Gly Ile Gly Val Pro Gly Ile Gly Val
            740                 745                 750
Pro Gly Ile Gly Ala Val Thr Gly Arg Gly Asp Ser Pro Ala Ser Ser
        755                 760                 765
Val Pro Gly Ile Gly Val Pro Gly Ile Gly Val Pro Gly Ile Gly Val
770                 775                 780
Pro Gly Ile Gly Val Pro Gly Ile Gly Val Pro Gly Ile Gly Val Pro
785                 790                 795                 800
Gly Ile Gly Val Pro Gly Ile Gly Val Pro Gly Ile Gly Val Pro Gly
                805                 810                 815
Ile Gly Val Pro Gly Ile Gly Val Pro Gly Ile Gly Val Pro Gly Ile
            820                 825                 830
Gly Val Pro Gly Ile Gly Val Pro Gly Ile Gly Val Pro Gly Ile Gly
        835                 840                 845
Val Pro Gly Ile Gly Val Pro Gly Ile Gly Val Pro Gly Ile Gly Val
    850                 855                 860
Pro Gly Ile Gly Ala Val Thr Gly Arg Gly Asp Ser Pro Ala Ser Ser
865                 870                 875                 880
Val Pro Gly Ile Gly Val Pro Gly Ile Gly Val Pro Gly Ile Gly Val
                885                 890                 895
Pro Gly Ile Gly Val Pro Gly Ile Gly Val Pro Gly Ile Gly Val Pro
            900                 905                 910
Gly Ile Gly Val Pro Gly Ile Gly Val Pro Gly Ile Gly Val Pro Gly
        915                 920                 925
Ile Gly Val
    930

<210> SEQ ID NO 26
<211> LENGTH: 5
<212> TYPE: PRT
<213> ORGANISM: Artificial Sequence
<220> FEATURE:
<223> OTHER INFORMATION: Synthetic construct of Sequence 3 of peptide B

<400> SEQUENCE: 26

Val Pro Ala Ile Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic construct of Alternative sequence 4
      of peptide B

<400> SEQUENCE: 27

Val Gly Ile Pro Ala
1               5
```

BIOPOLYMER, IMPLANT COMPRISING IT AND USES THEREOF

IN THE CROSS-REFERENCE TO RELATED APPLICATIONS

This application claims priority to Spanish Application No. P200900438, filed on Feb. 16, 2009, which is hereby incorporated by reference in its entirety for all purposes.

CROSS REFERENCE TO SEQUENCE LISTING

The peptides, proteins, and oligonucleotides described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

The present invention refers to a bioactive and wholly biocompatible biopolymer that is highly fluid at room temperature and has the ability to suddenly gel at 37° C., forming a structurally integral and continual solid implant with high mechanical properties. The biopolymer comprises at least one bioactive domain that is able to accurately control the formation of a solid or semi-solid implant. Likewise, the invention refers to any of the nucleic acids that code for the amino acid sequence of the biopolymer, implants, pharmaceutically acceptable vehicles, their uses and a synthetic method for it.

PRIOR STATE OF THE ART

Implants of solid macroscopic biomedical materials can be classified into two categories: (1) implants with no structural or continual integrity, and (2) materials that form a structurally continual or integral implant. The former strategy is based on implants of micro- or nanoparticles suspended in a biocompatible vehicle (Gamisans et al., 1999. *Int J Pharm,* 79: 37-48; Igartua et al., 1998. *J Control Rel;* 56: 63-73; Brannon-Peppas L, 1995. *Controlled release of ®-estradiol from biodegradable microparticles within silicone matrix; In: Polymer Biomaterials in Solution, as Interfaces and as Solids.* 1st ed. Utrecht (The Netherlands): VSP-Utrecht; Kawaguchi H, 2000. *Prog Polym Sci,* 25: 1171-1210). As they do not possess mechanical properties, such implants can migrate from the insertion site. Systems that combine a low viscosity with high fluidity at injection with a notable increase in the mechanical properties a posteriori, which results in the formation of a solid implant with well-defined borders, have therefore been designed to overcome this disadvantage.

The currently available families of injectable biomaterials can be classified into a) thermoplastic pastes, b) in situ precipitation, c) systems that are polymerisable or cross-linkable in situ, d) smart materials and e) combined strategy systems.

Thermoplastic pastes that present a viscosity increase are low molecular weight materials with a low glass transition temperature (Tg) and a melting temperature (Tm) of between 37° C. and 65° C.

Thus, these pastes are injected in molten form (generally at a temperature above body temperature) and slow crystallisation within the body results in solidification and the formation of a continuous implant (Hatefi et al., 2002. *J Control Rel,* 80: 9-28). The most important polymers for the development of such implants are polycaprolactone (PCL), polylactic (PLA), polyglycolic (PGA) and polydioxanone acids (PDO) and polyorthoesters (POEs), amongst others.

Sosnik and Cohn designed a modification of this strategy by synthesising block oligomers of polyethylene glycol and PCL that combined improved injectability with gradual hardening at 37° C. with time (Sosnik et al., 2003. *Polymer,* 44: 7033-7042).

Smart materials are those that display a sudden change in one of their properties (for example viscosity) in the event of a small change in their surroundings. The stimulus may be physical (e.g. temperature, ionic strength, magnetic or electric field, mechanical stress), chemical (e.g. pH) or biochemical (e.g. enzyme substrate or specific ligands (Hoffman et al., 2000. *J Biomed Mater Res Part A,* 52: 577-586).

Aqueous solutions of smart materials have low viscosity at room temperature and exhibit an increase upon heating, forming a semi-solid or solid gel when body temperature is reached. This transition usually occurs in a narrow temperature range. Various polymers are known to present such behaviour. These include poly-N-isopropylacrylamide (PNIPAAm) (Peppas et al., 2000. *Eur J Pharm Biopharm,* 50: 27-46), block copolymers of poly(ethylene oxide)-poly(propylene oxide) (PEO-PPO) (Bromberg et al., 1998. *Adv Drug Del Rev,* 31: 197-221), block copolymers of poly(ethylene oxide)-polyesters (PEO-PLA, PEO-PCL) (Jeong et al., 1999. *J Control Rel,* 62: 109-114) and other amphiphilic molecules designed by alternating hydrophilic and hydrophobic segments (Lee et al., 2002. *Macromolecules,* 35: 3876-3879). One of the main disadvantages presented by commercial PEO- and PPO-based polymers is the non-degradability of the polyether chain in biological media.

Combination of the previous techniques has led to implants that present properties of two of the above-mentioned groups of materials: (1) an increased viscosity with increased temperature and (2) covalent cross-linking to obtain robust mechanical properties and greater structural stability. Thus, the implant can be inserted in a liquid form, gelled at 37° C. to form a semi-solid gel and finally stabilised by covalent cross-linking. These polymers are often accompanied by solvents and organic reagents. The most important drawbacks of poly-N-isopropylacrylamides (PNIPAAm), which are some of the most common inverse thermosensitive polymers, include the non-degradability of pure matrices and the volume loss or contraction during heating.

It is known that elastin-like recombinamers (ELR), which are often used as biocompatible polymers, are highly versatile as these characteristics can be modified and extended by inserting amino acids from functional domains extracted from other proteins or de novo natural designs (Rodríguez-Cabello J C, Prieto S, Reguera J, Arias F J and Ribeiro A. (2007). *J. Biomater. Sci. Polymer Edn,* 18(3): 269-286). Said review also notes that the potential shown by ELR-based polymers has been expanded by the use of recombinant DNA technologies. This review discusses the current status of ELR polymers, with a particular emphasis on biomedical applications.

It is also known that peptides containing bioactive domains such as, for example, RGD (R=L-arginine, G=glycine and D=L-aspartic acid) or REDV (E=L-glutamic acid and V=L-valine), which provide these polymers with a high ability to bind to various cell types, can be inserted into the biopolymer chain.

Another family of materials of particular importance in this context are the PEO- and PPO-based block copolymers, known commercially as Pluronic (linear and bifunctional) and Tetronic (branched and tetrafunctional), which do not undergo a volume contraction like PNIPAAm but which, in contrast, do not achieve sufficiently high levels of viscosity for the majority of clinical applications even in those cases where the commercial materials undergo a sol-gel transition. In other words, the mechanical properties of PEO- and PPO-based polymers are unsatisfactory and their gels are excessively permeable to water, thus meaning that their residence times at the implant site are particularly short. For this reason, and in similar situations, combined strategies are frequently applied in order to prevent reabsorption of the implant immediately after insertion by markedly increasing the viscosity and subsequent covalent cross-linking to achieve robust mechanical properties and greater stability. This allows the formation of hydrogels with a modulus of 415 kPa but with a corresponding increase in the amount of time required to reach the desired consistency (often more than one hour) as the cross-linking reaction must occur under physiological conditions in this case.

Although numerous different ELR protein-based structures have been tested, a biopolymer that does not present a marked dilution of the implant is yet to be achieved. This is due above all to the fact that the gelation of such polymers is still too slow. This dilution of the implant reduces its efficacy.

The difficulties encountered in achieving a sufficiently fast and selective gelling process that produces an effective solid implant are therefore still to be overcome.

DESCRIPTION OF THE INVENTION

The present invention refers to a bioactive and biocompatible biopolymer that is highly fluid at room temperature and has the ability to suddenly gel at 37° C., forming a structurally integral and continual solid implant with high mechanical properties. The biopolymer comprises at least one bioactive domain that is able to accurately govern the formation of a solid or semi-solid implant such that as well as forming the implant it presents biofunctionalities such as interaction with cells in the body or introduces them by acting as a cell therapy system (regenerative medicine); it may also act as a controlled drug-release system, induce inorganic nucleation etc. Likewise, the invention refers to any of the nucleic acids that code for the amino acid sequence of the biopolymer, implants, pharmaceutically acceptable vehicles, their uses and a synthetic method for it.

The biopolymer of the present invention is a copolymer as it is formed from various monomers. The term copolymer is a synonym of heteropolymer. The monomers are peptides of five amino acids (pentapeptides) that can be joined in different ways by means of chemical bonds.

Self-gelling systems with a high degree of efficacy, complexity, control and robustness are obtained in the present invention from elastin-like protein-based polymers. The biopolymers in the present invention have been achieved using the following tools:

A knowledge of the hydrophobic and elastic forces of the amino acids. This allows an accurate and quantitative control of how hydrophobic or hydrophilic each pentapetide in the biopolymer should be. On the basis of this understanding and the so-called inverse transition ($T_t$) phenomenon exhibited by such materials, self-gelling elastin-like biopolymers were constructed from structures with alternating hydrophilic pentapeptides and hydrophobic pentapeptides such that the interactions between the hydrophobic pentapeptides in aqueous solution are key to producing the desired self-gelling phenomenon above a certain temperature.

The use of recombinant DNA technology by cloning a nucleic acid sequence that codes for the amino acid sequence of the biopolymer of the present invention in a vector that is able to express said sequence. This approach makes use of the replication, transcription and translation machinery of the organisms to produce the biopolymers.

The biocompatibility of biopolymers based on ELP (Elastin-Like Polypeptide) polypeptide sequences. This is a useful characteristic for the development of systems that function in contact with living tissue or specific fluids. The immune system cannot distinguish ELPs from natural elastin, therefore their biocompatibility can be considered to be extreme.

Therefore, taking advantage of these tools, recombinant biopolymers (produced using recombinant DNA techniques) acquire the ability to self-assemble and allow the development of nanometre-scale systems. This new strategy produces systems and self-assembly properties with characteristics clearly superior to those described to date.

The biopolymers of the present invention present various advantages with respect to other copolymers known in the state of the art:

They contain at least one bioactive domain such that the biopolymer binds to the specific cells for which it has been designed and then undergoes gelation, giving a material with a compressive modulus of elasticity of around $10^5$ Pa.

The gelation time from administration of the biopolymer (normally by injection) is between 1 and 3 minutes at 37° C. for a biopolymer with a concentration of between 150 and 200 mg/mL.

Such a fast gelation is very important to prevent a marked dilution of the implant in a biological environment, which may reduce the efficacy of the implant. As the gelation occurs in such a short time interval, it is vital to direct the biopolymer to the specific tissue of interest in order to achieve a solid and selective implant.

The biopolymers can form a solid, structurally integral implant with high mechanical properties in only a few minutes with no need for cross-linking. The polymers may be applied in treatments for nerve tissue and spinal cord damage, treatments for bone and cartilage damage (including sequences able to induce inorganic nucleation), in the prevention of scarring (including anti-adhesion sequences such as, for example, SEQ ID NO: 1), in the treatment of necrosed varicose veins, to increase tissue, in disease treatment by way of controlled drug-release (included in said biopolymer). Indeed, the biopolymers of this invention may be able to include multiple functionalities simultaneously in a single biopolymer, which may lead to obvious advantages as a result of its biocompatibility.

In this sense, the first aspect of the present invention is a biopolymer that comprises the amino acid sequences A, B and C with the structure: $(A_n\text{-}B_m)_s\text{-}C_p$, where, A has the structure $(D_{t1}\text{-}E_{v1}\text{-}D_{t2})$ or the structure $(D_{t1}\text{-}E_{v2})$, where D is SEQ ID NO: 1; E is SEQ ID NO: 2; t1 and t2 have values of between 2 and 4; and v1 and v2 have values of between 1 and 5, B is selected from the list comprising SEQ ID NO: 3, SEQ ID NO: 4 or SEQ ID NO: 26. B may also be the sequence SEQ ID NO: 27.

C has the structure $(G_{w1}\text{-}H_{x1}\text{-}G_{w2})$ or $H_{x2}$, where G is SEQ ID NO: 5; H is an amino acid sequence consisting of a peptide selected from the list comprising RGD, LDT, SEQ ID NO: 7, SEQ ID NO: 8, SEQ ID NO: 9 or SEQ ID NO: 10, SEQ ID NO: 11, SEQ ID NO: 12, SEQ ID NO: 13, SEQ ID NO: 14, SEQ ID NO: 15 or SEQ ID NO: 16; w1 and w2 have values of between 5 and 15; and x1 and x2 have values of between 1 and 5, n has a value of between 5 and 15, m has a value of between 10 and 70,
s has a value of between 2 and 4, and
p has a value of between 1 and 5.

Amino acid sequence A is the hydrophobic block, amino acid sequence B is the hydrophilic block and amino acid sequence C is the bioactive block. This latter block comprises domains that are able to recognise specific sequences and interact with them, thereby allowing the biopolymer of this invention to approach the desired target cell.

t1 and t2 may have the same, or a different, value. v1 and v2 may have the same, or a different, value. w1 and w2 may have the same, or a different, value. x1 and x2 may have the same, or a different, value.

The sequence RGD is recognised by various cell types, sequence SEQ ID NO: 7 is recognised by endothelial cells, LDT, SEQ ID NO: 8, SEQ ID NO: 9 is present in laminin and is recognised by various cell types, SEQ ID NO: 10 is recognised by neurites, in other words any projection from the soma of a neuron, whether a dendrite or an axon. These sequences that form part of the biopolymer of this invention are recognised by their respective cell types and promote binding. Those biopolymers containing SEQ ID NO: 7, SEQ ID NO: 9 or SEQ ID NO: 10 may be used in treatments for vascular, nerve tissue or spinal cord damage, respectively.

The sequence SEQ ID NO: 11 has an affinity for calcium phosphate, SEQ ID NO: 12 has an affinity for gold, SEQ ID NO: 13 has an affinity for silver, SEQ ID NO: 14 has an affinity for platinum, SEQ ID NO: 15 has an affinity for silicon ($SiO_2$), SEQ ID NO: 16 has an affinity for calcium carbonate ($CaCO_3$). These sequences allow properties such as binding to the mineral part of bone, the introduction of detection elements and bactericidal ability, amongst others, to be incorporated into the biopolymer.

Amino acid sequence H may contain a peptide belonging to a sequence from a growth factor, a sequence that induces inorganic nucleation, an anti-adhesion sequence such as, but not limited to, SEQ ID NO: 1. Sequence H may code for an active agent or a therapeutic agent or a chemotherapeutic agent or a therapeutic antibody or a fragment of a therapeutic antibody.

A growth factor is a substance that is normally, but not limited to, of a proteinaceous nature. Amongst other functions, the main function of a growth factor is to stimulate cell proliferation. The sequence of the growth factor is selected from the list comprising the factors: transforming growth factor beta TGF-beta (for bone regeneration), fibroblast growth factor FGF or KGF, epidermal growth factor EGF or TGF-alpha, vascular endothelial growth factor VEGF, insulin-like growth factor ILGF, factors such as BMPs for bone or the factor TGF-β from the Sonic hedgehog gene family The inorganic nucleation inducing sequence is a peptide that is able to, but is not limited to, actively and efficiently promote the nucleation and growth of inorganic crystals under conditions in which such crystals would not form or would form with another structure in the absence of this sequence.

The anti-adhesion sequence is a peptide sequence that inhibits the specific interaction between the biopolymer containing it and at least one cell type.

In this sense, the biopolymers of the present invention present a gelation time that is instantaneous in some cases and very short in all cases: between 1 and 12 minutes for biopolymer A and 21 minutes for biopolymer B. This time is much shorter that that exhibited by the biopolymers described in the state of the art, which is usually of the order of several hours, in which a viscosity increase and an in situ covalent cross-linking are required in order for them to achieve robust mechanical properties and greater stability. In this manner, there is no appreciable dilution of the implant in its biological environment similar to that found for purely cross-linkable systems. Furthermore, mechanical properties with compressive moduli of the order of $10^5$ Pa are achieved (for both biopolymer A and biopolymer B), thus meaning that combined strategies, which have the drawback that they require more time to achieve optimal properties and the introduction of other agents that may affect the biocompatibility of the implant, can be avoided.

A preferred embodiment of the invention refers to the biopolymer where A has the structure ($D_{t1}$-$E_{v1}$-$D_{t2}$). In a further preferred embodiment of the biopolymer, C has the structure ($G_{w1}$-$H_{x1}$-$G_{w2}$). According to a further preferred embodiment of the biopolymer, amino acid sequence H contains the peptide RGD. In a further preferred embodiment of the biopolymer, the amino acid sequence H containing the peptide RGD is SEQ ID NO: 6.

In another preferred embodiment, amino acid sequence B is SEQ ID NO: 3.

In a still more preferred embodiment of the biopolymer, m has a value of between 55 and 65. A more preferred embodiment is the biopolymer comprising peptides B, D, E, G, D and H with the structure $[(D_2\text{-}E\text{-}D_2)_{10}\text{-}B_{60}]_2\text{-}(G_{10}\text{-}H\text{-}G_{10})_2$.

A further preferred embodiment refers to the biopolymer where amino acid sequence is SEQ ID NO: 4. According to a more preferred embodiment of the biopolymer, m has a value of between 15 and 25. A more preferred embodiment is the biopolymer comprising peptides B, D, E, G, D and H with the structure $[(D_2\text{-}E\text{-}D_2)_{10}\text{-}B_{20}]_2\text{-}(G_{10}\text{-}H\text{-}G_{10})_2$. The peptide resulting from inserting the amino acid valine (V) between the amino acids glycine (G) and alanine (A) in the sequence SEQ ID NO: 4 acts as a target for proteases and modulates the biodegradability of the polymer and is very appropriate, for example, for drug release or regenerative medicine.

In order to introduce the functionalities required for each application, the recombinant elastin-like protein-based biopolymers are designed and constructed to measure by joining together different peptides containing domains that are introduced in order to include each of the required characteristics. Thus, these domains are:

Domains with biomimetic functions. These include those domains that are able to introduce self-assembly and self-organising functions on a nano- and microscale which are required in order to induce a drastic change in their physical properties on increasing the temperature. This characteristic of the biopolymer is known as Reverse Thermal Gelation (RTG). Aqueous solutions of these biopolymers have a low viscosity at room temperature and exhibit a viscosity increase as the temperature increases, forming a semi-solid or solid gel at body temperature (around 37° C.). As well as being responsible for the self-gelling behaviour, this characteristic allows the use of these biopolymers as drug dosing systems as the gelation process allows the encapsulation of drugs and active ingredients present in the solution that can subsequently be released in a controlled manner. Another type of application would be to increase tissue volume.

Non-bioactive elastin-like domain. Their role is to provide the material with the appropriate biocompatibility and mechanical properties. A biopolymer that only includes this type of sequence, with no bioactive sequences, could also be designed as an anti-adhesion system for applications such as adhesion prevention.

Bioactive domains. Those domains provide the biopolymer with specific cell-adhesion properties by way of known peptides from extracellular matrix proteins. As noted above, sequences with domains of this type include SEQ ID NO: 7, which is recognised by endothelial cells, LDT, SEQ ID NO: 8, SEQ ID NO: 9, which is obtained from laminin, or SEQ ID NO: 10, which is recognised by neurites.

Other domains for inducing biodegradability of the polymer that are highly suitable for producing controlled drug release.

The two above-mentioned biopolymers will hereinafter be referred to as "biopolymers of the invention" or "biopolymers of the present invention".

In accordance with the structures described above that lead to the biopolymers of the invention, the amino acid sequences (the term "peptides" may be used interchangeably to refer to the amino acid sequences) B, D, E, G and H may be joined by a covalent bond or any other type of bond that leads to a structure which maintains the properties of the biopolymers of the present invention. Said bond may be selected from, but is not limited to, the list comprising hydrogen bonds, ion pairing, hydrophobic association or inclusion complex formation.

Another aspect of the present invention refers to a nucleic acid containing a nucleotide sequence that codes for the amino acid sequence of any biopolymer of the invention.

The nucleic acid (hereinafter nucleic acid of the invention or nucleic acid of the present invention) includes nucleic acid sequences whose transcription product, messenger RNA (mRNA), codes for the same amino acid sequence (hereinafter amino acid sequence of the invention or amino acid sequence of the present invention). Variant degenerate sequences obtained from the nucleotide sequences of the invention whose product is a biopolymer with the same characteristics as the biopolymer of the invention are also included. Nucleotide sequences that code for amino acid sequences that contain modifications at their N-terminal end, C-terminal end and/or an internal amino acid position such that the function of the resulting biopolymer is the same as that resulting from translation of the mRNA sequence transcribed from the nucleotide sequence of the invention are also included. The amino acid sequence may be coded by any nucleotide sequence that leads to any of the amino acid sequences of the invention. As the genetic code is degenerate, a single amino acid may be coded by different codons (triplets), therefore the same amino acid sequence may be coded by different nucleotide sequences.

The nucleic acid of the present invention may have a nucleotide sequence that serves as a transcription initiation sequence bound at its 5' end. The sequence may be, but is not limited to, the nucleotide sequence SEQ ID NO: 20. Likewise, the nucleic acid of the present invention may have a transcription termination sequence such as, but not limited to, the sequence GTATGA bound to its 3' end.

A further aspect of the present invention refers to an expression vector comprising the nucleic acid of the invention.

The term "expression vector" (hereinafter vector of the invention or vector of the present invention) refers to a DNA fragment that is able to replicate itself in a certain host and, as the term suggests, may serve as a vehicle for multiplying another DNA fragment (insert) fused to it. Insert refers to a DNA fragment that is fused to the vector; in the case of the present invention, the vector may comprise any of the nucleotide sequences that code for any of the biopolymers of the invention, fused to it, that may replicate itself in an appropriate host. The vectors may be plasmids, cosmids, bacteriophages or viral vectors, without excluding any other type of vector that corresponds to the given definition of a vector.

Another aspect of the present invention refers to an isolated cell transfected with the vector of the invention. Such cells will hereinafter be referred to as "cells of the invention" or "cells of the present invention".

The term cell, as used in the present invention, refers to a prokaryotic or eukaryotic cell. The cell may be a bacteria capable of replicating a transformed external DNA, such as any of the strains of the species *Escherichia coli*, or a bacteria capable of transferring the DNA of interest to the interior of a plant, such as *Agrobacterium tumefaciens*. Preferably the cell refers to a eukaryotic plant cell, and within this group, more preferably, to those cells belonging to the kingdom Plantae. Thus, in the case where the cell is a plant cell, the term cell comprises at least a parenchymal cell, a meristematic cell or any type of differentiated or undifferentiated cell. Likewise, a protoplast (a plant cell lacking a cell wall) is also covered by this definition.

The term "transfection" refers to the introduction of external genetic material into cell using plasmids, viral vectors (the term transduction is also used in this case) or other transfer tools. For non-viral methods, the term transfection is used to refer to eukaryotic mammalian cells, whereas the term transformation is preferred to describe the non-viral transfer of genetic material in bacteria and non-animal eukaryotic cells such as fungi, alga or plants.

Another aspect of the present invention refers to the use of the biopolymer of the invention to prepare an implant. The term "implant", as used in the present invention, refers to a solid or semi-solid substance that can be placed inside the body to improve one or more of its functions, or for aesthetic purposes.

A further aspect of the present invention is an implant comprising any of the biopolymers of the invention. A preferred embodiment of the present invention is an implant where the biopolymer has a concentration of between 30 and 300 mg/mL. Preferably the implant has a biopolymer concentration of between 50 and 200 mg/mL. Another preferred embodiment of the invention is an implant that is presented in a form suitable for parenteral administration. A form suitable for parenteral administration refers to a physical state that allows administration by injection, in other words preferably in the liquid state, and thus requires that the biopolymer be at a temperature lower than its gelation temperature. Parenteral administration may be by the intramuscular, intradermal, subcutaneous or intraosteal administration route although it is not limited to these types of parenteral administration route. A further possibility is that the implant is presented in a form adapted to the administration route selected from the group comprising, but not limited to, oral, rectal, buccal, topical, nasal, ophthalmic, subcutaneous, intramuscular, intravenous, transdermal, intrathecal, intra-articular, intra-arterial, subarachnoid, bronchial, lymphatic, vaginal or intrauterine.

According to another preferred embodiment, the implant also includes an active substance. Said active substance is preferably a pharmaceutically acceptable substance used to prevent, diagnose, relieve, treat or cure diseases in animals. Said animal is preferably a mammal. Said mammal is preferably human. The implant may be mixed with cells of one or more types prior to its implantation.

The implant will hereinafter be referred to as "implant of the invention" or "implant of the present invention".

Another aspect of the present invention refers to the use of the implant of the invention to treat cartilage or bone. Defects that are not harmful may be treated using the implant. The treatment may involve damage prevention or simply an improvement of a state that does not imply damage. The implant is able to repair cartilage or bone damage or to maintain cartilaginous or bony structures fragmented at a macroscopic or microscopic level together, and also allows the release of pharmaceutically acceptable active substances that help to treat pain or to repair damage.

A further aspect of the present invention is the use of the implant of the invention to treat nerve or spinal cord tissue. Defects that are not harmful may be treated using the implant. The treatment may involve damage prevention or simply an improvement of a state that does not imply damage. The implant allows the release of pharmaceutically acceptable active substances that help treat pain or repair damage to nerve or spinal cord tissue. To undertake this type of treatment, the biopolymer may contain the sequence SEQ ID NO: 10 with incorporated cells. The incorporated cells may be stem cells, mesenchymal cells or any differentiated cell.

A further aspect of the present invention is the use of the implant to treat necrosed varicose veins. The biopolymer of the invention acts by blocking varicose veins, thereby causing them to necrose. The implant may contain pharmacological agents.

Another aspect of the present invention refers to the use of the biopolymer of the invention to prepare a medicinal product. A preferred embodiment refers to the use of the biopolymer of the invention to prepare a medicinal product for the treatment of cartilage and bone, the treatment of nerve or spinal cord tissue or the treatment of necrosed varicose veins.

A further aspect of the present invention refers to a pharmaceutically acceptable vehicle comprising any of the biopolymers of the invention.

As understood in the present invention, a "pharmaceutically acceptable vehicle" refers to those substances, or combinations of substances, known in the pharmaceutical sector and used for the preparation of pharmaceutical administration forms that include solids or liquids, solvents, detergents, etc. The pharmaceutically acceptable vehicle of the present invention allows a specific and targeted release or administration and also provides shape and consistency to the pharmaceutical preparation. Furthermore, the vehicle must be pharmaceutically acceptable, in other words allow the activity of the biopolymer of the invention.

A preferred embodiment is the pharmaceutically acceptable vehicle wherein the biopolymer of the invention has a concentration of between 30 and 300 mg/mL. The vehicle preferably has a biopolymer concentration of between 50 and 200 mg/mL. According to another preferred embodiment, the pharmaceutically acceptable vehicle is presented in a form suitable for parenteral administration. Furthermore, the type of administration may be selected from those mentioned in the previous section.

The pharmaceutically acceptable vehicle will hereinafter be referred to as the "vehicle of the invention" or "vehicle of the present invention".

Another aspect of the present invention refers to the use of the vehicle of the invention for controlled drug release. The vehicle is able to release a drug in a sustained and/or localised manner in a specific tissue or cell environment. The vehicle of the present invention may comprise an active substance. As described in the present invention, the biopolymer contained in the vehicle of the invention may contain cell-recognition sequences that provide a specific localisation. The vehicle of the present invention may be of, but is not limited to, a nanoparticle, microparticle, microsphere or microcapsule type. The vehicle of the invention may be used for controlled drug release in animals. Said animals are preferably mammals. Said mammals are preferably human.

The vehicle of the present invention capable of releasing drugs in a controlled manner may be used for, but is not limited to, the treatment of varicose veins.

A further aspect of the present invention refers to a method for synthesising the biopolymer of the invention that involves:
  a. inserting the nucleic acid of the invention into an expression vector,
  b. transfecting a cell with the expression vector obtained according to section (a),
  c. selecting the transfected cell according to section (b) that comprises the nucleic acid of the invention,
  d. expressing the nucleic acid in the cell according to section (c) and
  e. purifying the biopolymer produced according to section (d).

The degree of compositional complexity imposed by the need for a multifunctional design cannot be achieved using standard macromolecular synthesis techniques. The biopolymer is obtained as a recombinant protein in genetically modified microorganisms or plants using modified molecular biological and biotechnological techniques.

The nucleotide sequence that codes for the amino acid sequence of the biopolymer of the present invention is inserted into a previously defined expression vector.

Cell transfection, as defined in a previous paragraph, is undertaken using known techniques in the state of the art, for example, but not limited to, electroporation, biolistics, *Agrobacterium tumefaciens* or any other technique that allows the incorporation of the nucleic acids of the invention into the DNA of the host cell, whether it be genomic, chloroplastic or mitochondrial.

Expression of the nucleic acid in the cell of the invention leads to a biopolymer that can be purified using known techniques in the state of the art.

The word "comprises", and its variants, as used throughout the description and claims, is not intended to exclude other technical characteristics, additives, components or steps. For experts in the matter, other objects, advantages and characteristics of the invention will partially follow from the description and partially from the practice of the invention. The following figures and examples are provided by way of illustration and are not intended to limit the present invention.

The left-hand y-axis shows the values corresponding to G' (white circles) and the right-hand axis shows the values corresponding to G" (black circles); all values are in Pascals (Pa).

The Delta scale refers to the phase lag, measured in degrees.

The x-axis shows the temperature (T) in ° C.

Figure 3:
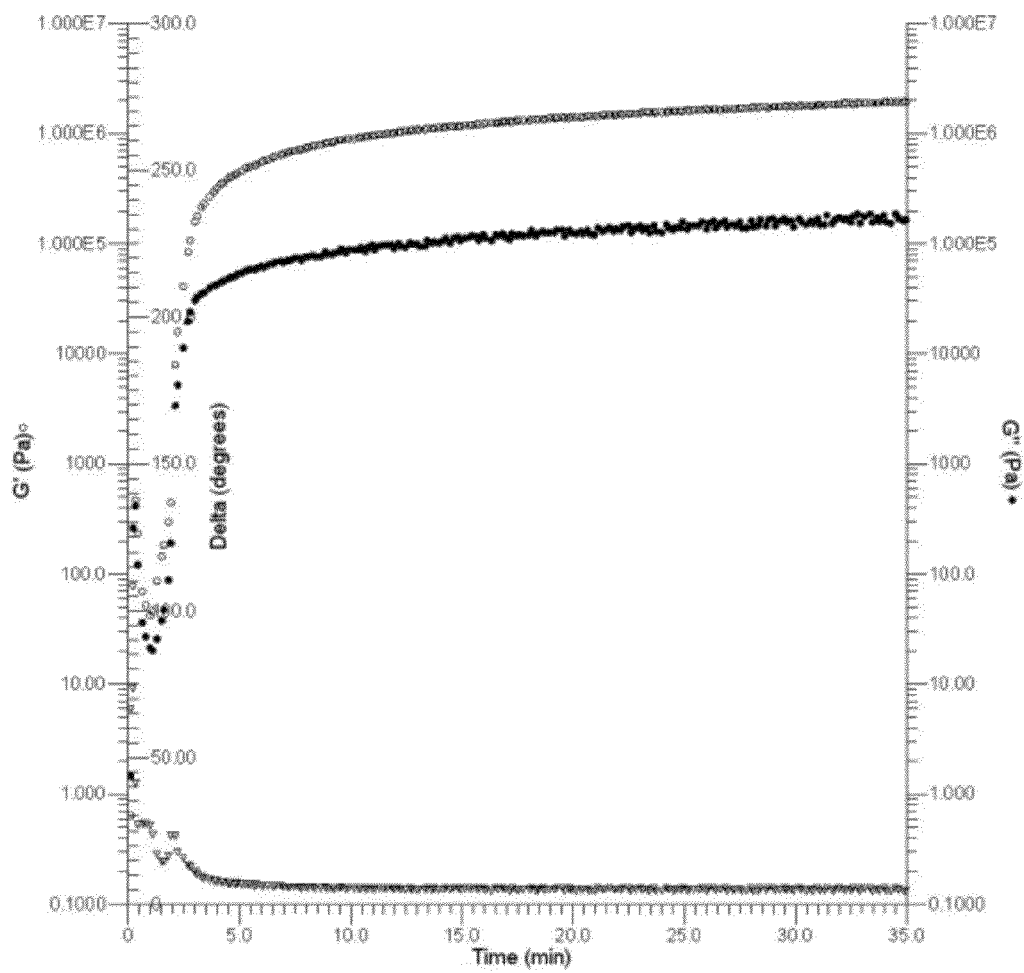

FIG. 3. Shows the change in the rheological properties of a sample of biopolymer A in PBS at a concentration of 200 mg/mL at 37° C.

The left-hand y-axis shows the values corresponding to G' (white circles) and the right-hand axis shows the values corresponding to G" (black circles); all values are in Pascals (Pa).

The Delta scale refers to the phase lag, measured in degrees.

The x-axis shows the time (t) in minutes.

Figure 4:
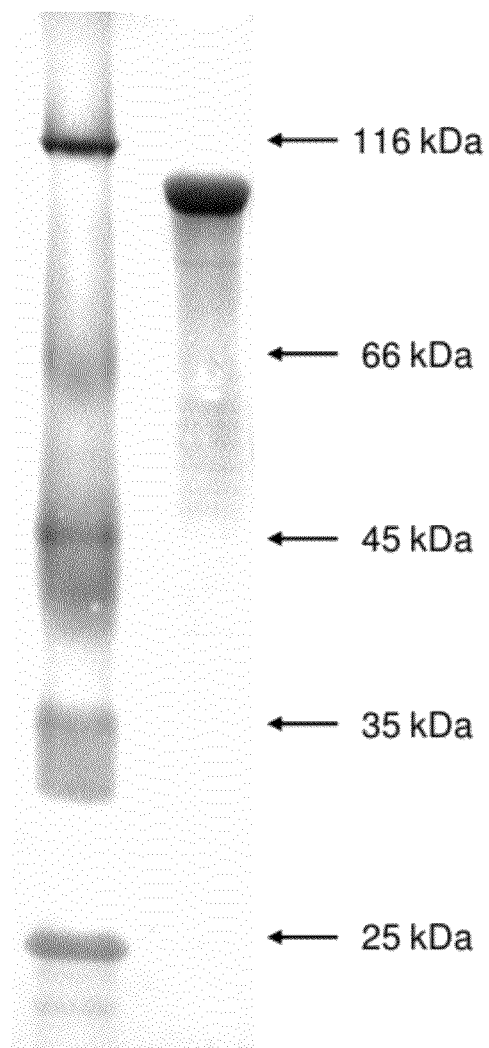

FIG. 4. Shows the SDS-PAGE electrophoresis for biopolymer B.

Figure 5:
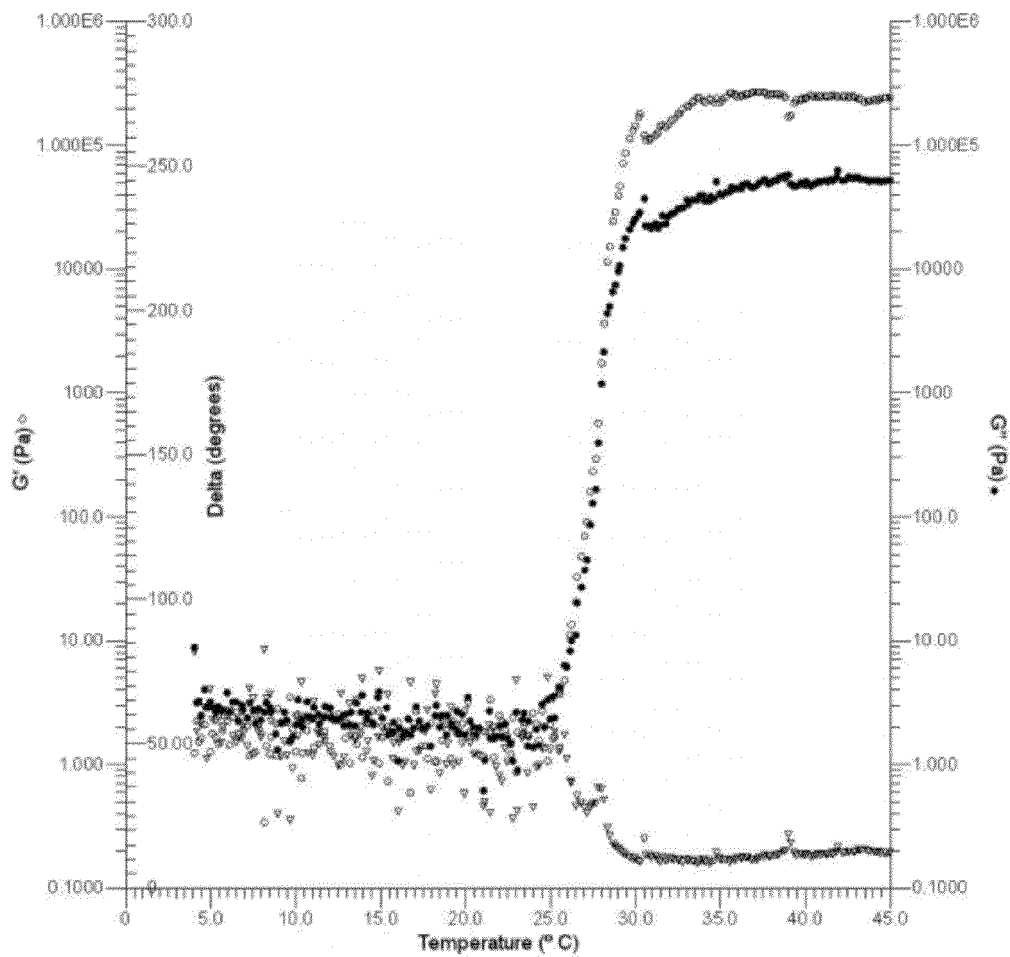

FIG. 5. Shows the dependence of the rheological properties of the polymer on temperature for a sample of biopolymer B in PBS at a concentration of 200 mg/mL.

The left-hand y-axis shows the values corresponding to G' (white circles) and the right-hand axis shows the values corresponding to G" (black circles); all values are in Pascals (Pa).

The Delta scale refers to the phase lag, measured in degrees.

The x-axis shows the temperature (T) in ° C.

Figure 6:
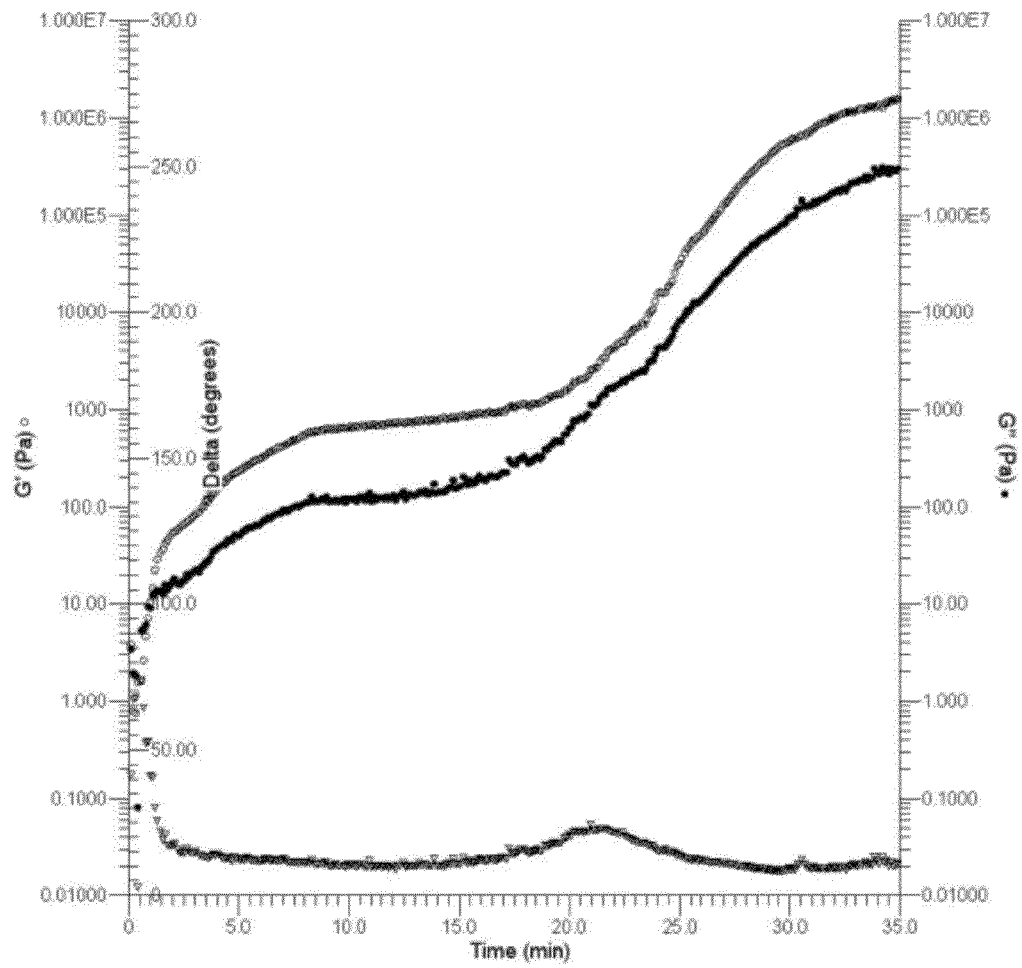

FIG. 6. Shows the change in the rheological properties of a sample of biopolymer B in PBS at a concentration of 200 mg/mL at 37° C.

The left-hand y-axis shows the values corresponding to G' (white circles) and the right-hand axis shows the values corresponding to G" (black circles); all values are in Pascals (Pa).

The Delta scale refers to the phase lag, measured in degrees.

The x-axis shows the time (t) in minutes.

Figure 7:
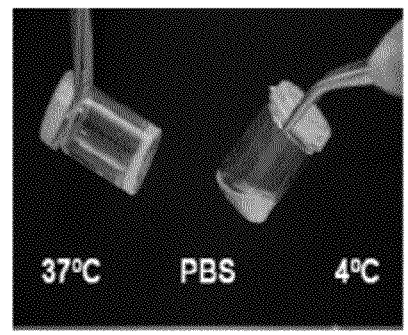
Figure 7:
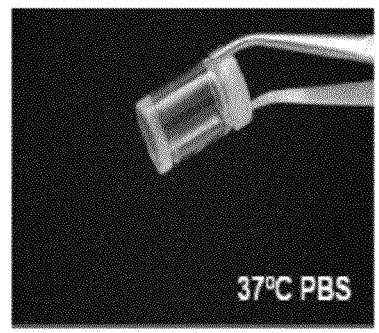
Figure 7:
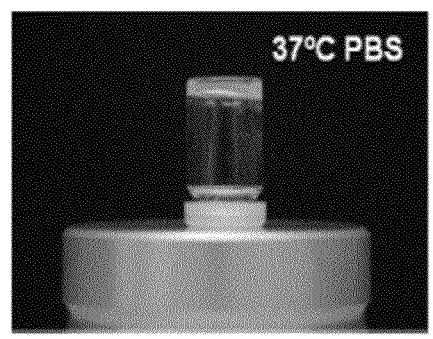

FIG. 7. Shows the biopolymers of the invention dissolved in PBS below (4° C.) and above (37° C.) their transition temperature.

Figure 8:
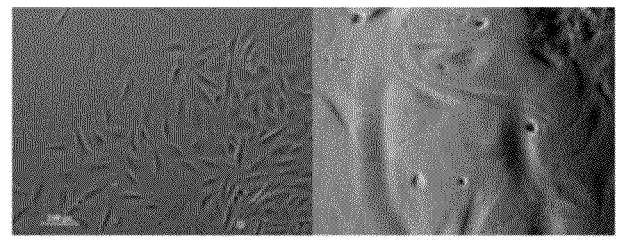

FIG. 8. Shows images of fibroblasts seeded on fibronectin obtained two hours post-seeding.

Figure 9:
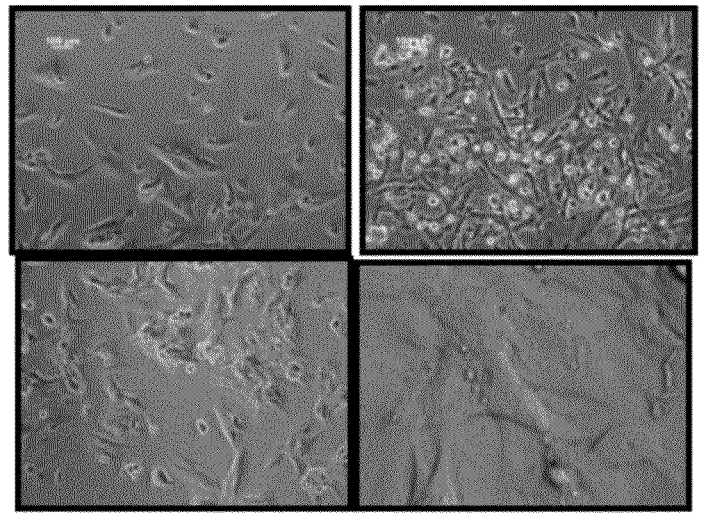

FIG. 9: Shows images of fibroblasts seeded on self-gelling elastin-like copolymer A obtained two hours post-seeding.

Figure 10:
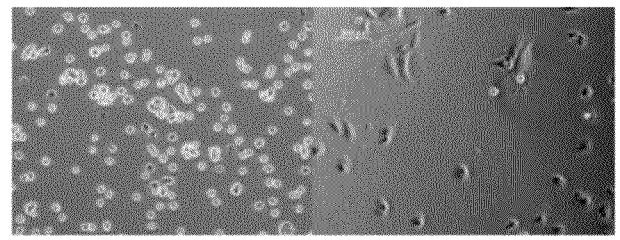

FIG. 10: Shows images of fibroblasts seeded on BSA obtained two hours post-seeding.

Figure 11:
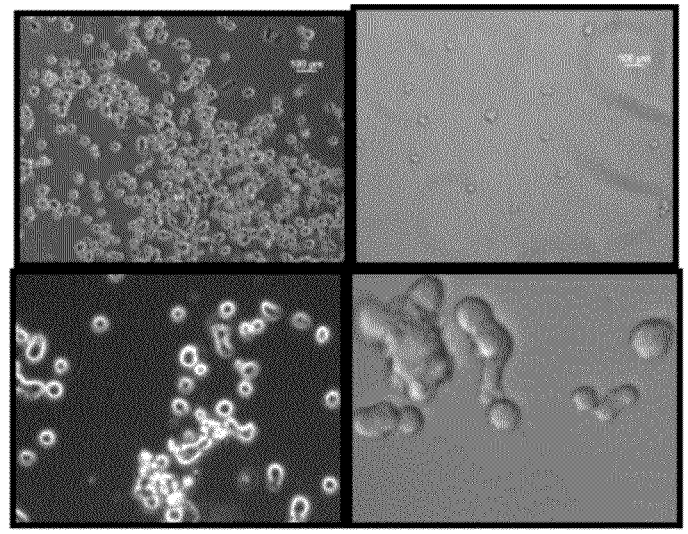

FIG. 11: Shows images of fibroblasts seeded on the control self-gelling elastin-like copolymer obtained two hours post-seeding.

Figure 12:
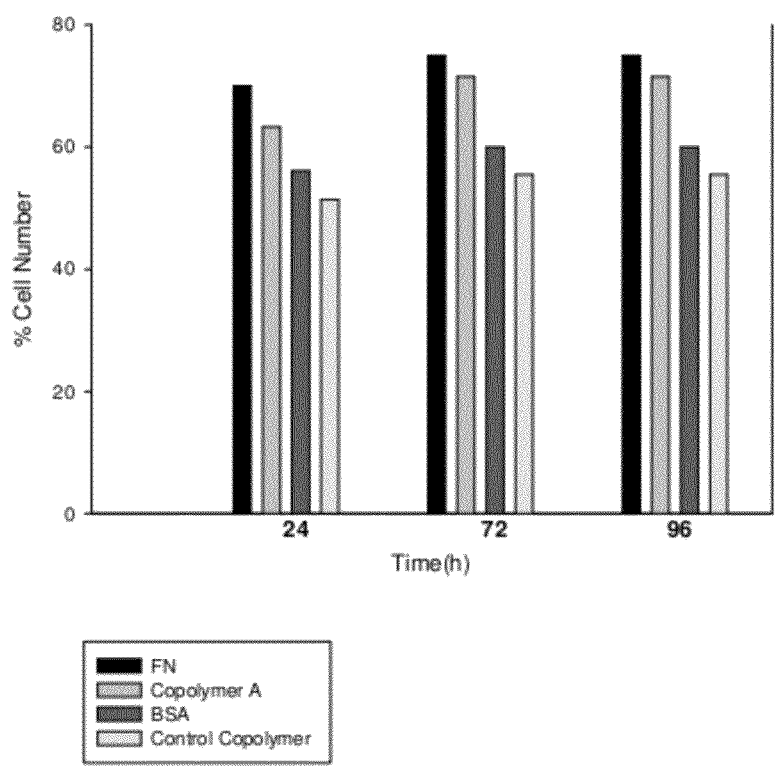

FIG. 12. Shows the percentage of cells from the culture medium grown on different substrates for 24, 72 and 96 hours. FN indicates fibronectin and BSA bovine serum albumin.

Figure 13:
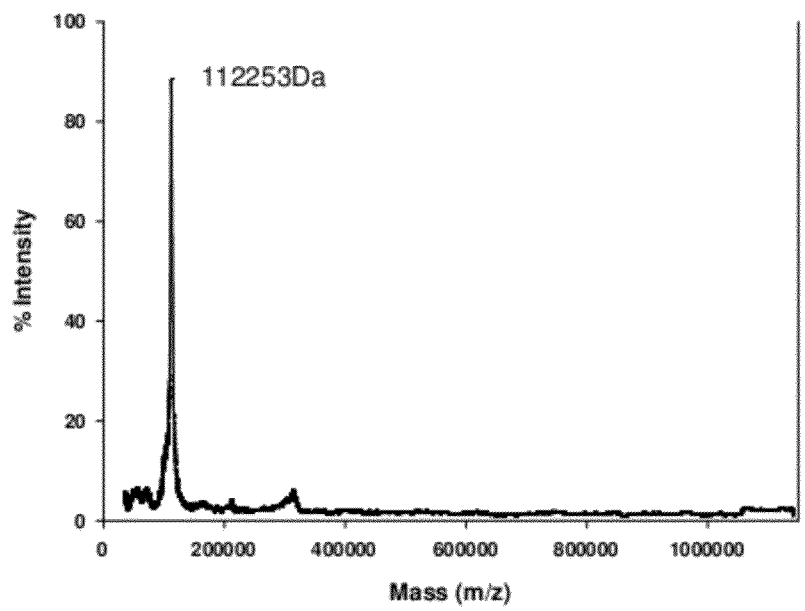

FIG. 13. Shows the mass spectrum for one of the spots analysed with self-gelling elastin-like copolymer A.

Figure 14:
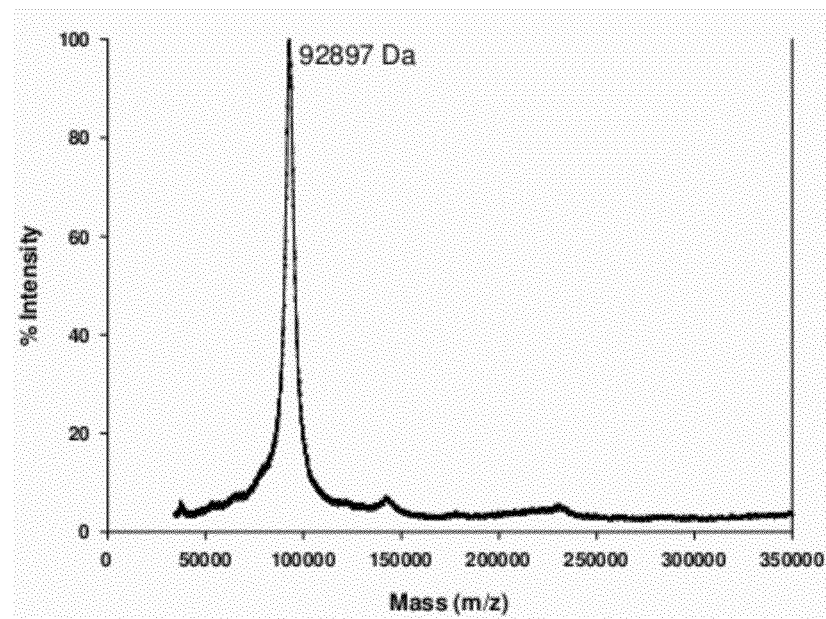

FIG. 14. Shows the mass spectrum for one of the spots analysed with the control self-gelling elastin-like copolymer.

EXAMPLES

The invention is illustrated below by way of various trials undertaken by the inventors that describe the synthesis of the biopolymer of the present invention and its rheological characteristics. Said examples are provided in order to be able to understand the description and are not intended to limit the present invention.

Example 1

Production of Recombinant Elastin-Like Protein-Based Polymers 1.1 Design and Production of the Synthetic Nucleotide Sequence that Codes for the Amino Acid Sequence of the Biopolymer of the Invention At the gene design stage it proved necessary to try to overcome the contradiction that exists between the use of the most common and appropriate codons that identify highly repeated amino acids and the need not to overload or even impoverish the cell translation system to the point of collapse. If heterologous prokaryotic systems are used, the problem arising from their limited use of the genetic code, which varies with species, must be taken into account. The problem arising from the creation of a gene formed by a long sequence that codes for multiple and/or small artificial fragments was also taken into account. Finally, the high recombination frequency commonly found when the exogenous DNA contains repeats of highly similar domains also had to be overcome.

This stage involved the use of automated DNA synthesisers together with recombinant DNA techniques. The production of polymers with multiple repeats necessarily involves the production of a gene that codes for them which, depending on the length of the sequence, may require the prior synthesis of a polynucleotide-based monomer that can be connected linearly in the correct direction.

The production of sufficient amounts of the monomeric gene containing the correct sequence for producing the repeat nucleotide sequences that code for the various polypeptides required culture of the appropriate clones and digestion of their plasmids. This allowed the large amount of monomer required for the controlled ligation, concatenation or concatenamerisation reaction to be obtained in a simple manner.

Although this approach may appear to be wasteful in terms of time, in vivo synthesis guarantees the production of the correct sequence in large amounts and also offers additional advantages, such as control of the monomeric gene prior to oligomerisation and the ability to subsequently modify the sequence by either directed mutagenesis or by the creation of copolymers prior to oligomerisation.

Polymerisation of the monomeric nucleotide sequences may be undertaken by, but is not limited to, concatenation, in other words random ligation of the monomeric blocks; the iterative/recursive method, a step-by-step technique for preparing oligomers from monomers; or by the Seamless cloning method, a definition that refers to the possibility to select a specific sequence that is translated into the desired amino acid at the cut-off point.

Concatenation allows the synthesis of polymers from oligomers by the unidirectional, linear head-to-tail attachment of the DNA segments that make up the monomer, although such attachment is only possible if the ends of the segments are single-stranded, protuberant and cohesive amongst themselves but not with themselves. Thus, the single-stranded head end of the monomer will be complementary to, and will only hybridise with, the tail end of another identical monomer. These ends cannot therefore be palindromic, as currently occurs when they are generated by the restriction endonucleases routinely used in genetic engineering, where the recognition and cleavage sites occur sequentially, but must be different.

Various modifications of the concatenation technique have been developed to take into account specific requirements. Monomers with cohesive, single-stranded ends were obtained by the hybridisation of oligomers, by the joining of short oligonucleotides (linkers) and also by digestion with specific endonucleases.

The iterative/recursive method is a step-by-step technique used to prepare oligomers from monomers that allows both the addition sequence and the number of blocks to be joined during each growth stage to be controlled, thereby allowing ad hoc polymer production. This method requires the creation of sequences at the ends of the segment that code for the protein-based monomer, are recognised by two different endonucleases and whose cleavage produces complementary, but not palindromic, ends. This monomeric sequence is cloned in a plasmid that serves as a gene amplification vector and provides both the following cloning vector when digested with a single enzyme and the clone insert when cleaved by two enzymes.

The Seamless cloning method removes the relationship between the design of the sequence for the insert that codes for the monomer and the sequences recognised by the endonucleases that generate it. This strategy is possible due to the existence of a limited number of type II restriction enzymes that recognise a specific, non-palindromic sequence that does not coincide with the cleavage site. This unique characteristic eliminates the drawbacks resulting from the need to include unusual sequences into the polymer in order to allow the generation of cohesive ends that allow concatenation and also means that fragments that join in a unidirectional manner can be achieved in a single digestion.

1.2. Polymer Expression and Purification

One the nucleotide sequence that codes for the whole biopolymer has been created, it must be expressed. To this end, the nucleotide sequence was transferred from the corresponding cloning vector to the specialised expression vector using conventional restriction enzymes. Once it had been confirmed that this transfer had occurred correctly, a specific bacterial strain for the expression of said sequence was transformed using any of the valid techniques found in the common general knowledge.

Expression of the recombinant polypeptides was initiated by inoculating an isolated colony containing the corresponding recombinant vector in liquid LB medium with the eventual resistance antibiotic for the strain and the acquired resistance antibiotic with the expression vector.

The bacterial culture was incubated at 37° C., with orbital shaking at 250 rpm, for approximately 11 hours, then this culture broth was used to inoculate a fresh medium in a 1/30 ratio. The mean volume in the Erlenmeyers did not exceed 20-25% of their capacity in order to ensure good oxygenation of the culture, and bacterial growth was continued under the same conditions until an optical density of around 0.6 at 600 nm had been achieved. At that point expression of the recombinant biopolymer was induced by adding isopropyl β-D-1-thiogalactopyranoside (IPTG) to a final concentration of 1 mM, and the resulting culture was incubated at the appropriate temperature for the time required for each experiment.

Once induction was complete, further growth and metabolism of the bacteria were inhibited by cooling to 4° C. The cells were subsequently sedimented by centrifuging for 10 min at 5000 g and 4° C., the supernatant was decanted off and the walls of the centrifuge tubes dried to remove any traces of culture medium.

The sediment was washed with 100 mL/L of culture in Tris buffered saline (TBS; Tris-base 20 mM, NaCl 150 mM pH 8), the bacteria resuspended by vigorous stirring and/or pipetting and the mixture centrifuged again for 10 min at 5000 g and 4° C. The supernatant was then decanted and the sediment resuspended in 25 mL/L of culture with TE solution (Tris-base 20 mM, EDTA 1 mM pH 8) by vigorous stirring and/or pipetting. The resulting mixture was maintained at 4° C. and 10 μg/mL of the protease inhibitor phenylmethylsulfonyl fluoride (PMSF) added.

The bacteria were lysed by sonication in a Sonicator 3000 apparatus (Misonix, N.Y.) for 6 cycles of 3.5 minutes, each consisting of pulses of 2 seconds every 5 seconds at a power of around 100 W. The sample was maintained on ice throughout this process in order to prevent heat-induced denaturation and precipitation of the proteins. Finally, it was centrifuged for 60 minutes at 15,000 g and 4° C., with the resulting supernatant containing the total soluble fraction and the sediment the total insoluble fraction. The total soluble fraction of the bacteria was acidified to pH 3.5 with hydrochloric acid diluted in water, maintaining the sample on ice and stirring. The resulting precipitate (mainly acid proteins and DNA) was then removed by centrifugation for 20 minutes at 15,000 g and 4° C. Depending on the polymer concerned, the saline concentration and pH of the supernatant were adjusted.

The polymers were purified by taking advantage of the smart nature of elastin-like polymers and their inverse transition. Purification of the recombinant polymers from the soluble fraction of *E. coli* involves successive heating/precipitation and cooling/resuspension stages. Selective precipitation was performed by heating the sample to 70° C. for two hours. The precipitate was then separated by centrifuging for 20 minutes at 15,000 g and 40° C., and solubilised in 2 mL/L of type I water at 4° C. whilst stirring for 12 hours. This procedure was repeated twice more. After the final solubilisation, the dissolved polymer was dialysed against type I water at 4° C., then lyophilised and stored at −20° C.

Example 2

Production of Recombinant Elastin-Like Protein-Based Polymers A

As a first example, an elastin-like copolymer A with the ability to self-assemble due to the fact that it contains alternating blocks with a hydrophobic and hydrophilic nature, which means that its mechanical properties change drastically above the inverse transition temperature, is described. In this case the hydrophobic blocks correspond to type B peptides where the amino acid sequence is SEQ ID NO: 3 and the hydrophilic blocks to peptides of the type $[(D)_2(E)(D)_2]$. Furthermore, the amino acid sequence C includes a non-specific bioactive RGD sequence. In other words, the biopolymer of this example has the structure: $[(D_2\text{-}E\text{-}D_2)_{10}\text{-}B_{60}]_2\text{-}(G_{10}\text{-}H\text{-}G_{10})_2$

2.1. Synthesis of the Synthetic Nucleotide Sequence that Codes for Biopolymer A The polymer was synthesised as described in example 1. To synthesise the hydrophilic block of 25 amino acids ($D_2$-E-$D_2$), an artificial nucleotide sequence was generated by hybridising two complementary oligonucleotides with the sequence SEQ ID NO: 17.

In order to ensure that the above monomeric sequence could be concatenated to form the complete sequence, appropriate restriction enzyme recognition sequences that, when used, leave only the GTA codon, which codes for the amino acid valine, as the cohesive ends, were placed at its ends. This ensures that monomer chains with no skips in the reading frame or codons other than those contained in the desired sequence are formed.

Using the concatenation technique, a nucleotide sequence consisting of 10 repeats of the initial sequence, with a coding region of 750 base pairs and flanked by the restriction sequences and GTA linker codons, was obtained.

Synthesis of the hydrophilic block started with a larger initial fragment, although this was also synthesised chemically from oligonucleotides. In this case the peptide-based monomer had the structure $(B)_{20}$ where B is SEQ ID NO: 3, which is coded by the nucleotide sequence SEQ ID NO: 18.

The same restriction enzymes, and therefore the same flanking sequences for the coding gene, were also used in this example, although in this case the recursive/iterative method was used to repeat the described gene three times and form a gene 900 base pairs in length that codes for 60 repeats of the B-type pentablock.

The nucleotide sequence of the hydrophilic block described $(D_2-E-D_2)_{10}$ and that corresponding to the hydrophobic block $(B)_{60}$ where B is SEQ ID NO: 3, were fused using the above-mentioned restriction sequences, placing the gene that codes for the hydrophilic block at the 5' end. The resulting sequence, with a length of 1650 base pairs, was subsequently duplicated using the recursive technique to give a sequence 3300 base pairs in length that codes for the polypeptide $(D_2-E-D_2)_{10}-(B)_{60}$ The bioactive sequence was incorporated using the same described technique.

In this case, the sequence that codes for the structure $(G_{10}-H-G_{10})$ is SEQ ID NO: 19.

In this case, the fragment was also duplicated using the same described techniques before joining it to the 1650-base pair tetrablock. The product of this duplication has a length of 672 base pairs coding for a polypeptide of 224 amino acids. Incorporation of the two bioactive RGD sequences at the 3' end of the 3330-base pair fragment was performed using the iterative/recursive technique and the restriction enzymes mentioned above.

Said incorporation resulted in a sequence of 3972 base pairs that codes for the abbreviated polypeptide: $[D_2-E-D_2]_{10}-[B]_{60}-[D_2-E-D_2]_{10}[B]_{60}-[(G)_{10}-H-(G)_{10}]-[(G)_{10}-H-(G)_{10}]$ This sequence was incorporated into an expression vector previously modified to accept fragments produced by digestion with the described appropriate restriction enzymes incorporating the nucleotide sequence SEQ ID NO: 20 at the 5' end of the 3972-base pair fragment and the sequence GTATGA at its 3' end. The resulting plasmid comprises a nucleotide sequence with an open reading frame of 3996 base pairs, SEQ ID NO: 21, which codes for 1331 amino acids, SEQ ID NO: 22.

2.2 Expression of Recombinant Biopolymer A

The expression vector was used to transform a strain of *Escherichia coli* suitable for expressing the exogenous genes by selecting the transforming colonies using the appropriate antibiotic.

One of the colonies resulting from this transformation was used to inoculate a volume of LB medium with the same antibiotic and 1% glucose. After incubation at 37° C. with orbital shaking at 250 rpm overnight, the bacterial culture was used to inoculate a 100-fold larger volume of TB medium with the same antibiotic and a concentration of 0.8% (v/v) glycerol, 0.2% (w/v) alpha-lactose and 0.05% (w/v) glucose.

After incubation under the same conditions, the resulting cells were isolated by centrifugation and washed twice with saline buffer. They were then resuspended in EDTA-containing buffer, and PMSF was added to a final concentration of 1 mM. The suspended cells were sonicated at 4° C. and the extract centrifuges to remove bacterial remains.

The supernatant of this bacterial extract was submitted to various cycles of heating at 60° C., centrifugation, collection of the sediment and solubilisation at 4° C. in EDTA-containing buffer. Each purification stage was checked by polyacrylamide electrophoresis in the presence of SDS. Once the polymer was considered to be sufficiently pure, it was dialysed against type I water and lyophilised. The resulting lyophilised polymer was stored in a cold, dry place until use.

2.3. Characterisation of Elastin-Like Biopolymer A

Figure 1:
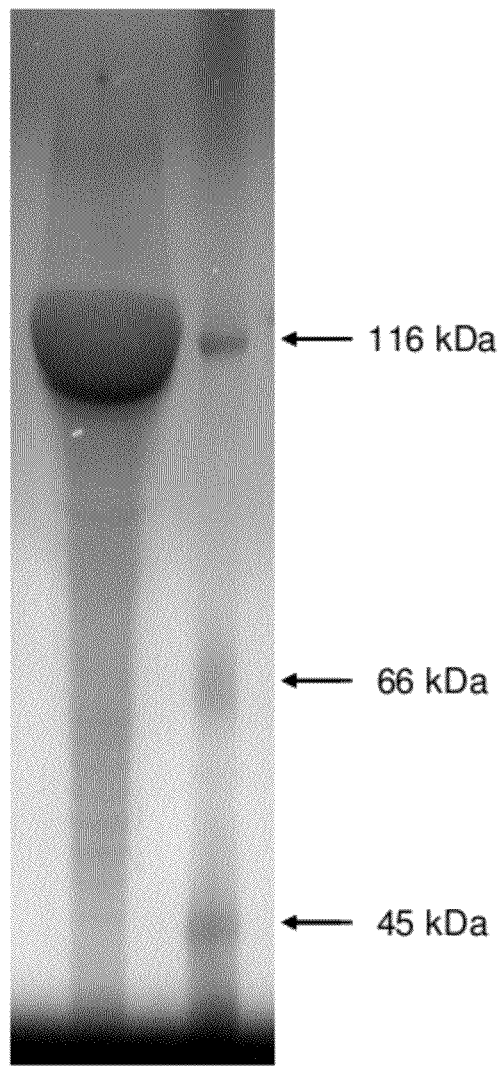
FIG. 1. Shows the SDS-PAGE electrophoresis for biopolymer A.
Figure 2:
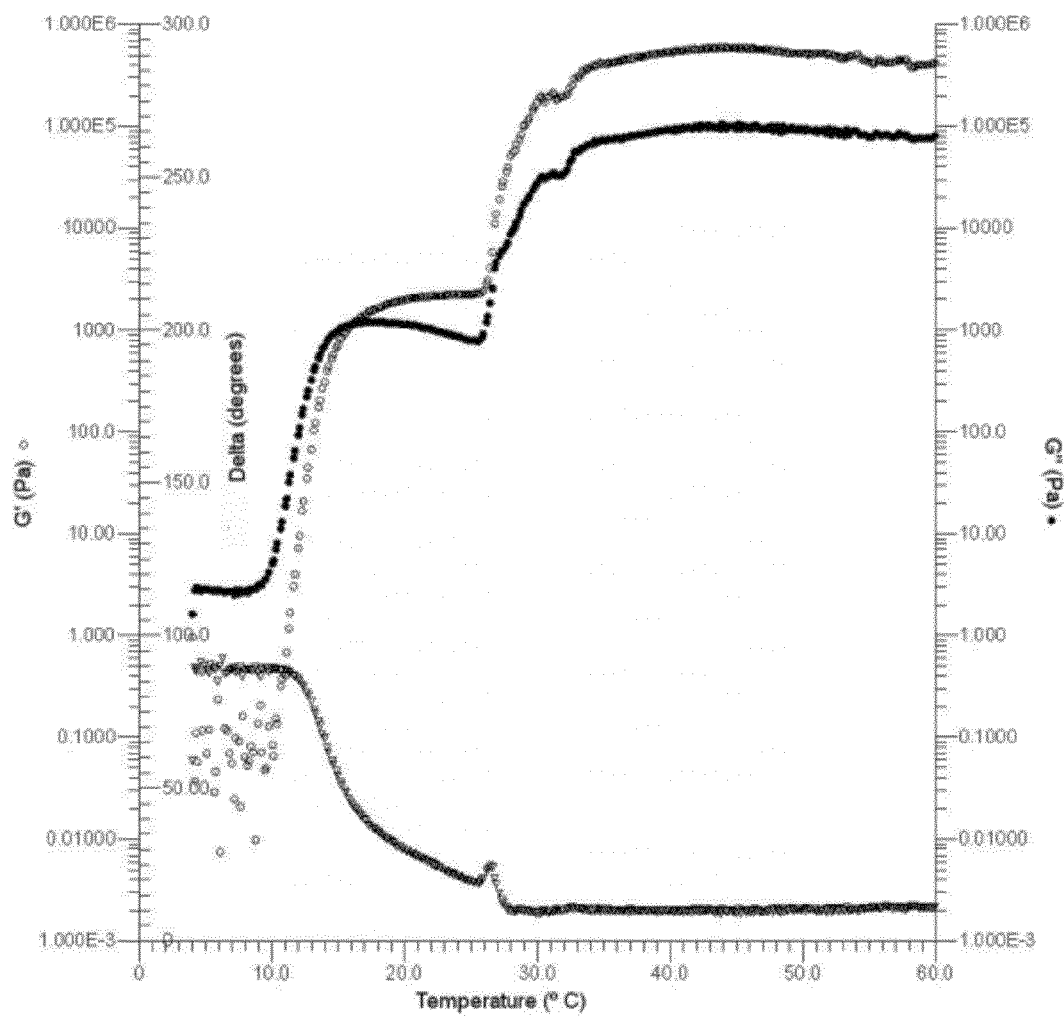
FIG. 2. Shows the dependence of the rheological properties of the polymer on temperature for a sample of biopolymer A in PBS at a concentration of 200 mg/mL.

Biopolymer A was characterised by polyacrylamide gel electrophoresis (PAGE) in the presence of SDS, which allowed the molecular weight of the polymer to be estimated and its purity to be confirmed. The left lane in FIG. 1 corresponds to the sample and the right lane to the markers (Fermentas SM0431). It can be seen from said figure that a good yield of electrophoretically pure polymer was obtained. The position of the polymer band coincides with that of the 116 kDa marker, therefore biopolymer A has this apparent molecular weight.

A MADLI-TOF mass spectrum was also recorded using a Q-Star spectrometer to determine the exact molecular weight of the polymer. Said analysis gave a molecular weight of 112,292 Da.

Physical characterisation of the material involved a rheological study. All experiments were performed with an AR2000ex (TA Instruments) controlled force rheometer using parallel plates with a gap of 250 µm. For gelation, the solutions were placed on a thermostatted Peltier plate. The linear viscoelasticity range was determined at a frequency of 1 Hz, selecting a deformation of 0.5% for the time and temperature scans within this range.

Samples of biopolymer A with a concentration of 50, 100, 150 and 200 mg/mL in PBS were prepared and heated from 4 to 60° C. at a rate of 1° C./min to determine their rheological properties. The gelation temperature was identified from the "gel point" ($T_{gel}$), which is defined as the point at which G' is equal to G" (Pilosof 2000).

As an example, FIG. shows the elastic, or storage, modulus (G'), the viscous, or loss, modulus (G") and the phase lag (delta) for the sample with a concentration of 200 mg/mL. The phase lag (delta) indicates the relationship between the elasticity and viscosity. A gelation temperature of 16° C. can be obtained from this figure, with restructuring commencing at 10° C. and the optimal mechanical properties being achieved at 26° C. The gelation temperature for the remaining concentrations is the same. It can therefore be concluded that the product achieves optimal mechanical properties after introduction into the body. Furthermore, Table 1 shows the values obtained for the elastic and viscous moduli and the phase lag for the different concentrations tested. It can be deduced from these values that the mechanical properties of the material diminish from the highest sample concentration to the lowest. Thus, the value of G' for the 200 mg/mL sample is $3.0 \times 10^5$ Pa and that for the 50 mg/mL sample is $5.7 \times 10^4$.

As mentioned above, another characteristic of vital importance is the time required by the system to gel at body temperature post-injection, in other words the time required for it to self-assemble and for its mechanical properties, especially its viscosity, to change in order to prevent its dispersal inside the body. In this sense, and in order to determine the gelation kinetics, rheological experiments were performed in isothermal mode at 37° C. in order to study the changes in the rheological properties of the solutions of copolymer A in PBS with time. FIG. 3 shows the results obtained for the sample with a concentration of 200 mg/mL. As can be seen from this figure, heating times longer than 4 minutes did not significantly affect the values of the loss and storage moduli, with gel formation being observed 2 minutes after placing the sample at 37° C.

Table 1 also contains data regarding the injectability of the samples with different sized needles. G20 and G26 needles were tested and it was found that all samples up to a concentration of 150 mg/mL could readily be injected using needles with a diameter up to G26, whereas samples with a concentration of 200 mg/mL proved difficult to inject, thus meaning that needles with a diameter of G20 had to be used.

TABLE 1

Rheological and injectability data for solutions of self-gelling elastin-like bipolymer A in PBS at different concentrations.

| Concentration | $t_{gel}$ (min) | G' (Pa) | G" (Pa) | Phase lag | Complex viscosity $\eta^*$ (Pa.s) | Injectability G20 | Injectability G26 |
|---|---|---|---|---|---|---|---|
| 200 mg/mL | 1 | $3.0 \times 10^5$ | $8.5 \times 10^4$ | 4-5 | 7-9 | Easy | Difficult |
| 150 mg/mL | 9 | $1.0 \times 10^5$ | $1.5 \times 10^4$ | 11-12 | 3-5 | Very easy | Easy |
| 100 mg/mL | 11 | $6.4 \times 10^4$ | $1.4 \times 10^4$ | 7-8 | 0.7 | Very easy | Easy |
| 50 mg/mL | 12 | $5.7 \times 10^4$ | $8.8 \times 10^4$ | 8-9 | 0.2 | Very easy | Very easy |

Example 3

Production of Recombinant Elastin-Like Protein-Based Polymers B

As a first example, an elastin-like copolymer B with the ability to self-assemble due to the fact that it contains alternating blocks with a hydrophobic and hydrophilic nature, which means that its mechanical properties change drastically above the inverse transition temperature, is described. In this case the hydrophobic blocks correspond to type B peptides where the amino acid sequence is SEQ ID NO: 4 and the hydrophilic blocks to peptides of the type $[(D)_2(E)(D)_2]$. Furthermore, the amino acid sequence C includes a non-specific bioactive RGD sequence. In other words, the biopolymer of this example has the structure: $[(D_2-E-D_2)_{10}-B_{20}]_2-(G_{10}-H-G_{10})_2$ 3.1. Synthesis of the Synthetic Nucleotide Sequence that Codes for Biopolymer B The polymer was synthesised as described in example 1. To synthesise the hydrophilic block of 25 amino acids ($D_2$-E-$D_2$), an artificial nucleotide sequence was generated by hybridising two complementary oligonucleotides with the sequence SEQ ID NO: 17.

In order to ensure that the above monomeric sequence could be concatenated to form the complete sequence, appropriate restriction enzyme recognition sequences that, when used, leave only the GTA codon, which codes for the amino acid valine, as the cohesive ends, were placed at its ends. This ensures that monomer chains with no skips in the reading frame or codons other than those contained in the desired sequence are formed.

Using the concatenation technique, a nucleotide sequence consisting of 10 repeats of the initial sequence, with a coding region of 750 base pairs and flanked by the restriction sequences and GTA linker codons, was obtained.

Synthesis of the hydrophilic block started with a larger initial fragment, although this was also synthesised chemically from oligonucleotides. In this case the peptide-based monomer had the structure $(B)_{20}$ where B is SEQ ID NO: 4, which is coded by the nucleotide sequence SEQ ID NO: 23.

The same restriction enzymes, and therefore the same flanking sequences for the coding gene, were also used in this case. The nucleotide sequence of the hydrophilic block described $(D_2-E-D_2)_{10}$ and that corresponding to the hydrophobic block $(B)_{20}$ where C is SEQ ID NO: 4, were fused using the above-mentioned restriction sequences, placing the gene that codes for the hydrophilic block at the 5' end. The resulting sequence, with a length of 1050 base pairs, was subsequently duplicated using the recursive technique to give a sequence 2100 base pairs in length that codes for the polypeptide $[(D_2-E-D_2)_{10}-(B)_{20}]_2$ The bioactive sequence was incorporated using the same described technique.

The sequence that codes for the structure $(G_{10}-H-G_{10})$ is SEQ ID NO: 19.

In this case, the fragment was also duplicated using the same described techniques before joining it to the 2100-base pair tetrablock. The product of this duplication has a length of 672 base pairs coding for a polypeptide of 224 amino acids. Incorporation of the two bioactive RGD sequences at the 3' end of the 2100-base pair fragment was performed using the iterative/recursive technique and the restriction enzymes mentioned above.

Said incorporation resulted in a sequence of 2772 base pairs that codes for the abbreviated polypeptide: $[D_2-E-D_2]_{10}[B]_{20}-[D_2-E-D_2]_{10}-[B]_{20}-[(G)_{10}-H-(G)_{10}]-[(G)_{10}-H-(G)_{10}]$ where B is SEQ ID NO: 4.

This sequence was incorporated into an expression vector previously modified to accept fragments produced by digestion with the described appropriate restriction enzymes incorporating the nucleotide sequence SEQ ID NO: 20 at the 5' end of the 2772-base pair fragment and the sequence GTATGA at its 3' end. The resulting plasmid comprises a nucleotide sequence with an open reading frame of 2796 base pairs, SEQ ID NO: 24, which codes for 931 amino acids, SEQ ID NO: 25.

3.2 Characterisation of Elastin-Like Biopolymer B

Recombinant biopolymer B was expressed in the same manner as described in example 2.2.

Likewise, as described in example 2, an acrylamide gel electrophoresis (PAGE) was carried out in the presence of SDS. The right lane in FIG. 4 corresponds to the sample and the left lane to the markers (Fermentas SM0431). It can be seen from said figure that a good yield of electrophoretically pure polymer was obtained. The position of the polymer band allowed us to estimate the molecular weight of this polymer to be between 75 and 85 kDa.

A MADLI-TOF mass spectrum was also recorded using a Q-Star spectrometer to determine the exact molecular weight of the polymer. Said analysis led to a value of 78,379 Da.

As in the previous case, physical characterisation of the material involved a rheological study. All experiments were performed with an AR2000ex (TA Instruments, Spain) controlled force rheometer using parallel plates with a gap of 250 μm. For gelation, the solutions were placed on a thermostatted Peltier plate. The linear viscoelasticity range was determined at a frequency of 1 Hz, selecting a deformation of 0.5% for the time and temperature scans within this range.

Samples with a concentration of 200 mg/mL in PBS were prepared and heated from 4 to 60° C. at a rate of 1° C./min to determine their rheological properties. The gelation temperature was identified from the "gel point" ($T_{gel}$), which is defined as the point at which G' is equal to G" (Pilosof 2000).

The elastic, or storage, modulus (G'), the viscous, or loss, modulus (G") and the phase lag (delta) for the solution of copolymer B with respect to temperature are shown in FIG. 5. A gelation temperature of 29° C. can be obtained from this figure, with restructuring commencing at 25° C. and the optimal mechanical properties being achieved at 33° C. Although this temperature is lower than body temperature it is nevertheless close to it, therefore problems may arise in body regions where temperature decreases occur for whatever reason. Furthermore, Table 2 shows the values obtained for the elastic and viscous moduli and the phase lag. The value of G' ($2.5 \times 10^5$ Pa) is very close to that obtained for copolymer A ($3.0 \times 10^5$ Pa).

It can be seen from FIG. 6 that gel formation commenced 21 minutes ($t_{gel}$) after placing the sample at 37° C. and that it took 37 minutes for the optimal properties to be achieved, in other words the kinetics are notably slower than for biopolymer A.

Table 2 also contains data regarding the injectability of the samples with different sized needles. G20 and G26 needles were tested and it was found that the samples could easily be injected with both types. This finding is reasonable as the viscosity of the copolymer B solution at a concentration of 200 mg/mL is similar to that for solutions of copolymer A at a concentration of 50 mg/mL due to the fact that copolymer B has a lower molecular weight than copolymer A.

TABLE 2

Rheological and injectability data for solutions of self-gelling elastin-like bipolymer B in PBS.

| Concentration | $t_{gel}$ (min) | G' (Pa) | G" (Pa) | Phase lag | Complex viscosity $\eta^*$(Pa.s) | Injectability G20 | G26 |
|---|---|---|---|---|---|---|---|
| 200 mg/mL | 21 | $2.5 \times 10^5$ | $5.0 \times 10^4$ | 11-12 | 0.2-0.4 | Very easy | Very easy |

It can therefore be concluded from the results obtained with these two examples that the properties of copolymer B are slightly inferior to those of copolymer A presented in example 2. Although the elastic moduli obtained for these two copolymers are very similar, the gelation time and temperature are markedly higher for copolymer B in example 3.

FIG. 7 shows images of self-gelling elastin-like biopolymers dissolved in PBS solution at 4° C., in other words below their transition temperature, where they remain in solution, and at 37° C., in other words above their transition temperature, where gelation has occurred.

Example 4

Evaluation of the Interaction of Self-Gelling Elastin-Like Copolymers with Primary Cells The bioactivity introduced into self-gelling elastin-like copolymer A by the insertion of RGD cell-adhesion motifs was assessed by analysing the interaction between cells and the material in a primary human cell culture (fibroblasts).

Cell-adhesion tests were performed using substrates obtained from self-gelling elastin-like copolymer A, a control elastin-like copolymer with a similar composition but without the block containing the active sequence and standard protein-based substrates, with fibronectin, in other words a structural protein from the extracellular matrix that contains the integrin-mediated cell-adhesion motifs, as the positive control and non-specific BSA (bovine serum albumin), which does not induce cell adhesion, as the negative control.

The biopolymers in the present example therefore have the following structure: Self-gelling elastin-like copolymer A: $[(D_2\text{-}E\text{-}D_2)_{10}\text{-}B_{60}]_2\text{-}(G_{10}\text{-}H\text{-}G_{10})_2$ of example 2. Amino acid sequence A has the structure $(D_2\text{-}E\text{-}D_2)_{10}$, and amino acid sequence C has the structure $(G_{10}\text{-}H\text{-}G_{10})_2$. Amino acid sequence C includes a non-specific bioactive RGD sequence.

Control self-gelling elastin-like copolymer: $[(D_2\text{-}E\text{-}D_2)_{10}\text{-}B_{60}]_2$. This type of copolymer lacks the cell-adhesion domain that characterises this type of biopolymer, as defined in example 2 of the present invention.

The polymers to be tested were adsorbed onto polystyrene surfaces (a standard material for cell cultures) using solutions of them in PBS buffer with concentrations of 1 mg/mL. They were then washed several times with PBS and any unsaturated regions on the surface blocked with BSA protein.

After removal using a mild enzymatic and mechanical treatment, the fibroblasts were seeded onto them ($10^4$ cells/cm$^2$), incubated for 2 hours at 37° C. under a controlled atmosphere and their adhesion studied qualitatively and quantitatively. It was found that these cells interacted differently with the different substrates two hours post-seeding. Thus, the cells deposited on the positive control (fibronectin; FIG. 8) and on self-gelling elastin-like copolymer A (FIG. 9) acquired a similar morphology, as in both cases the cells bind to the surface and extend their cytoplasm. In contrast, the cells seeded on the negative control (BSA; FIG. 10) and on the control self-gelling elastin-like copolymer (FIG. 11), which lack bioactive motifs, barely interacted with the material, maintaining the spheroidal shape of the cells in suspension in both cases. It was also noted that washing the BSA and control self-gelling elastin-like copolymer surfaces with physiological buffer removed the vast majority of the absorbed cells from the, although no such effect was observed with self-gelling elastin-like copolymer A, which contains bioactive domains that induce a much stronger integrin-mediated interaction.

Spectrophotometry-based cytotoxicity or proliferation tests were also carried out using the "AlamarBlue™" detection system from AbD Serotec. FIG. 12 shows an estimation of the number of (metabolically active) cells present at 24 72 and 96 hours post-seeding. These findings demonstrate that none of the substrates are cytotoxic at the times studies as the number of active cells is maintained over the period of the experiment. It was also noted that the above-mentioned differences in terms of the good adhesion to self-gelling elastin-like copolymer A and the control polymer were observed during all stages of the experiment as the amount of cells present at 24, 72 and 96 hours post-seeding was notably higher for the copolymer A substrate than for the control polymer. Likewise, it should be noted that the bioactive copolymer A substrate showed the most similar behaviour to that of the positive control (fibronectin) as the estimated number of active cells on it was notably greater than that for the control copolymer and BSA substrates.

Development of the cell culture was also monitored under an inverted microscope, which confirmed that the fibroblast cultures achieved confluence on all substrates, although after different times depending on the number of cells bound in the first few hours post-seeding. The confluence time for the fibronectin and self-gelling elastin-like copolymer A substrates was lower than for the BSA and control self-gelling elastin-like copolymer substrates.

4.1. MALDI ToF Analysis

The MALDI ToF analysis was performed using a Reflex IV MALDI ToF spectrometer (Bruker, Bremen, Germany) equipped with a CovaIX HM2 detector for the mass range 0 to 1500 kDa. The instrument was calibrated externally using insulin, BSA and IgG clusters. A total of 3 spots (300 laser pulses per spot) were analysed for this sample. Data were analysed using the Complex Tracker software The main protein detected in the three spots for self-gelling elastin-like copolymer A had a molecular weight (MW) of 12,253±18 Da, which compares with the previous finding of 112,292 Da reported above, a variation of 0.03% that is perfectly acceptable for this technique.

The main protein detected in the three spots for the control self-gelling elastin-like copolymer had a molecular weight (MW) of 92,897±19 Da, which compares with the previous finding of 93,176 Da reported above, a variation of 0.3% that is perfectly acceptable for this technique.

The amino acid compositions of self-gelling elastin-like copolymer A and the control copolymer are presented in Table 3.

The amino acid composition was determined using the AccQ-Tag Waters method The derivatised amino acids were analysed by HPLC (High Performance Liquid Chromatography) with UV detection using a WATERS600 HPLC gradient system fitted with a WATERS2487 detector. The most representative amino acids were quantified using a 1/10 solution.

The results of the amino acid analysis correlate very well with the expected amino acid composition taking into account the endogenous errors of this technique and the particular composition of the sample

TABLE 3

Estimation and measurement of the amino acid composition for self-gelling elastin-like copolymer A (copolymer A) and the control self-gelling elastin-like copolymer (control copolymer).

|  | Control copolymer | | Copolymer A | |
| --- | --- | --- | --- | --- |
|  | Estimated | Experimental | Estimated | Experimental |
| Asp | 0 | 0.47 | 2 | 2.59 |
| Ser | 1 | 1.09 | 7 | 6.56 |
| Glu | 21 | 22.01 | 21 | 20.8 |
| Gly | 440 | 432.83 | 524 | 533.08 |
| Thr | 0 | 0.22 | 2 | 1.67 |
| Ala | 0 | 0.37 | 4 | 4.98 |
| Pro | 221 | 224.02 | 263 | 261.27 |
| Arg | 0 | 0 | 2 | 2.36 |
| Val | 301 | 304.8 | 343 | 350.15 |
| Lys | 0 | 0.22 | 0 | 0 |
| Ile | 120 | 119.34 | 160 | 145.5 |
| Met | 1 | 0.25 | 1 | 0.31 |
| Leu | 2 | 1.91 | 2 | 3.76 |

The invention claimed is:

1. A biopolymer containing the amino acid sequences A, B and C with the structure $(A_n\text{-}B_m)_s\text{-}C_P$, where, A has the structure $(D_{t1}\text{-}E_{v1}\text{-}D_{t2})$ or the structure $(D_{t1}\text{-}E_{v2})$, where D is SEQ ID NO: 1; E is SEQ ID NO: 2; t1 and t2 have values of between 2 and 4; and v1 and v2 have values of between 1 and 5, B is selected from the group consisting of SEQ ID NO: 3, SEQ ID NO: 4 and SEQ ID NO: 26 (VPAIG), C has the structure $(G_{w1}\text{-}H_{x1}\text{-}G_{w2})$ or $H_{x2}$, where G is SEQ ID NO: 5; H is an amino acid sequence consisting of a peptide selected from the group consisting of RGD, LDT, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16; w1 and w2 have values of between 5 and 15; and x1 and x2 have values of between 1 and 5, n has a value of between 5 and 15, m has a value of between 10 and 70, s has a value of between 2 and 4, and p has a value of between 1 and 5.

2. A biopolymer according to claim 1 where A has the structure $(D_{t1}\text{-}E_{v1}\text{-}D_{t2})$.

3. A biopolymer according to claim 1 where C has the structure $(G_{w1}\text{-}H_{x1}\text{-}G_{w2})$.

4. A biopolymer according to claim 2 where C has the structure $(G_{w1}\text{-}H_{x1}\text{-}G_{w2})$.

5. A biopolymer according to claim 1 where the amino acid sequence of H contains the peptide RGD.

6. A biopolymer according to claim 1 where the amino acid sequence of B is SEQ ID NO: 3.

7. A biopolymer according to claim 6 that consists of the structure $[(D_2\text{-}E\text{-}D_2)_{10}\text{-}B_{60}]_2\text{-}(G_{10}\text{-}H\text{-}G_{10})_2$.

8. A biopolymer according to claim 1 where peptide C is SEQ ID NO: 4.

9. A biopolymer according to claim 8 that consists of the structure $[(D_2\text{-}E\text{-}D_2)_{10}\text{-}B_{20}]_2\text{-}(G_{10}\text{-}H\text{-}G_{10})_2$.

10. A nucleic acid with a nucleotide sequence encoding for the amino acid sequence of the biopolymer according to claim 1; an expression vector containing said nucleic acid; or an isolated cell transfected with said expression vector.

11. A method for the preparation of an implant comprising the gelification of the biopolymer according to claim 1 at 37° C. to form a solid or semi-solid implant.

12. An implant comprising the biopolymer according to claim 1.

13. An implant according to claim 12, wherein the implant is in a form suitable for parenteral administration, and the implant further comprises an active substance.

14. A medicinal product comprising the biopolymer according to claim 1.

15. A method for the treatment of cartilage or bone, the treatment of nerve or spinal cord tissue, or for necrotizing of varicose veins in a subject comprising the administration of the biopolymer according to claim 1 to said subject.

16. A pharmaceutically acceptable vehicle comprising the biopolymer according to claim 1, wherein the vehicle comprises the biopolymer at a concentration of between 30 and 300 mg/mL; and the pharmaceutically acceptable vehicle is presented in a form suitable for parenteral administration.

17. A method for obtaining a biopolymer containing the amino acid sequences A, B and C with the structure $(A_n\text{-}B_m)_s\text{-}C_p$, where, A has the structure $(D_{t1}\text{-}E_{v1}\text{-}D_{t2})$ or the structure $(D_{t1}\text{-}E_{v2})$, where D is SEQ ID NO: 1; E is SEQ ID NO: 2; t1 and t2 have values of between 2 and 4; and v1 and v2 have values of between 1 and 5, B is selected from the group consisting of SEQ ID NO: 3, SEQ ID NO: 4 and SEQ ID NO: 26 (VPAIG), C has the structure $(G_{w1}\text{-}H_{x1}\text{-}G_{w2})$ or $H_{x2}$, where G is SEQ ID NO: 5; H is an amino acid sequence consisting of a peptide selected from the group consisting of RGD, LDT, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15 and SEQ ID NO: 16; w1 and w2 have values of between 5 and 15; and x1 and x2 have values of between 1 and 5, n has a value of between 5 and 15, m has a value of between 10 and 70, s has a value of between 2 and 4, and p has a value of between 1 and 5, the method comprising:

a. inserting the nucleic acid of claim 10 into an expression vector, b. transfecting a cell with the expression vector obtained according to section (a), c. selecting the transfected cell according to section (b) that comprises the nucleic acid of claim 10, d. expressing the nucleic acid in the cell according to section (c) and e. purifying the biopolymer produced according to section (d).

18. An implant according to claim 12 wherein the biopolymer concentration is between 30 and 300 mg/mL.

19. The pharmaceutically acceptable vehicle according to claim 16, wherein the pharmaceutically acceptable vehicle further comprises an active substance.

* * * * *